US012799132B2

(12) United States Patent
Xu et al.

(10) Patent No.: US 12,799,132 B2
(45) Date of Patent: Nov. 17, 2026

(54) CRYSTAL FORM OF URAT1 INHIBITOR PULIGINURAD AND PREPARATION THEREOF

(71) Applicant: SHANGHAI YINGLI PHARMACEUTICAL CO., LTD, Shanghai (CN)

(72) Inventors: Zusheng Xu, Shanghai (CN); Yangtong Lou, Shanghai (CN); Youhai Tang, Shanghai (CN)

(73) Assignee: SHANGHAI YINGLI PHARMACEUTICAL CO., LTD., Shanghai (CN)

( * ) Notice: Subject to any disclaimer, the term of this patent is extended or adjusted under 35 U.S.C. 154(b) by 288 days.

(21) Appl. No.: 18/725,904

(22) PCT Filed: Dec. 28, 2022

(86) PCT No.: PCT/CN2022/142594

§ 371 (c)(1),
(2) Date: Jul. 1, 2024

(87) PCT Pub. No.: WO2023/131017

PCT Pub. Date: Jul. 13, 2023

(65) Prior Publication Data

US 2025/0059202 A1 Feb. 20, 2025

(30) Foreign Application Priority Data

Jan. 4, 2022 (CN) ......................... 202210000887.9

(51) Int. Cl.
*C07D 495/04* (2006.01)
*A61K 31/4365* (2006.01)
*A61K 45/06* (2006.01)

(52) U.S. Cl.
CPC ........ *C07D 495/04* (2013.01); *A61K 31/4365* (2013.01); *A61K 45/06* (2013.01)

(58) Field of Classification Search
None
See application file for complete search history.

(56) References Cited

U.S. PATENT DOCUMENTS

2018/0072678 A1* 3/2018 Xu ............................ A61P 3/00
2018/0265476 A1 9/2018 Xu et al.

FOREIGN PATENT DOCUMENTS

CN 106008340 A 10/2016
WO 2016150255 A1 9/2016

OTHER PUBLICATIONS

International Preliminary Report on Patentability issued on Jun. 20, 2024, in corresponding International Application No. PCT/CN2022/142594, with English translation of the Report (10 pages).

International Search Report (PCT/ISA/210) issued on Apr. 24, 2023, by the China National Intellectual Property Administration (ISA/CN) in corresponding International Application No. PCT/CN2022/142594, with English translation of the Search Report (5 pages).

Opinion of Examination issued on Mar. 26, 2024, by the Taiwanese Patent Office in corresponding TW Application No. 112100279, with partial English translation of the Opinion (5 pages).

Zhang et al., "Application Progress of Drug Crystal Forms in Drug Research," Journal of Pharmaceutical Research, vol. 40, No. 4, pp. 266-271 (2021).

* cited by examiner

*Primary Examiner* — Jennifer A Berrios
*Assistant Examiner* — Sophia Reilly
(74) *Attorney, Agent, or Firm* — Panitch Schwarze Belisario & Nadel LLP

(57) ABSTRACT

Disclosed are a crystal form of a fused ring derivative, and a preparation method therefor and the use thereof. The crystal form I of the compound as represented by formula A has high purity and good stability, and is non-hygroscopic. In addition, the crystallization solvent used in the preparation method therefor has the advantage of low residue and is suitable for industrial production.

A

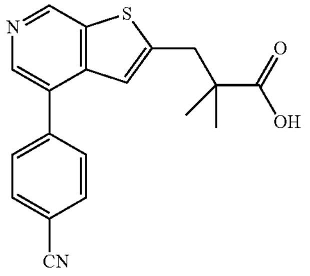

12 Claims, 9 Drawing Sheets

CRYSTAL FORM OF URAT1 INHIBITOR PULIGINURAD AND PREPARATION THEREOF

CROSS-REFERENCE TO RELATED APPLICATIONS

This application is a Section 371 of International Application No. PCT/CN2022/142594, filed Dec. 28, 2022, which was published in the Chinese language on Jul. 13, 2023, under International Publication No. WO 2023/131017 A1, which claims priority under 35 U.S.C. § 119(b) to Chinese Application No. 202210000887.9, filed Jan. 4, 2022, the disclosures of which are incorporated herein by reference in their entirety.

TECHNICAL FIELD

The present disclosure belongs to the field of pharmaceutical and specifically relates to a crystal form of a fused ring derivative 3-[4-(4-Cyanophenyl)thieno[2,3-c]pyridin-2-yl]-2,2-dimethylpropanoic acid, a preparation method therefor and the use thereof.

BACKGROUND

A fused ring derivative 3-[4-(4-Cyanophenyl)thieno[2,3-c]pyridin-2-yl]-2,2-dimethylpropanoic acid, with the molecular $C_{19}H_{16}N_2O_2S$, has structure shown in formula A

A

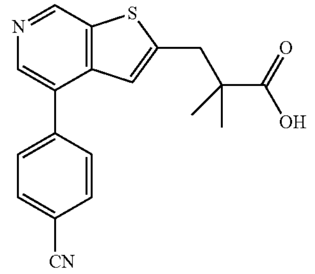

(hereinafter referred to the compound as represented by formula A), is a uric acid transporter 1 (short as URAT1) inhibitor, which can effectively alleviate and treat hyperuricemia and related diseases by inhibiting the reabsorption of uric acid at the proximal tubules of the kidney and promoting the excretion of uric acid out of the body through urine.

It is well known that the phenomenon of polymorphism of substances arises from two or more differently arranged crystal structures. Different crystal forms of compound tend to exhibit different physical and chemical properties. For drugs, different solid forms including anhydrate, hydrate, solvate and amorphous may have certain differences in physicochemical properties such as melting point, hygroscopicity, solubility, dissolution rate, mobility, compressibility, and stability. In order to ensure the safety, efficacy and quality consistency of drugs for clinical use, the polymorphism phenomenon of drugs needs to be fully investigated during the drug development process, and suitable solid form should be selected for clinical development of drugs.

Chinese patent CN106008340A discloses a class of fused ring derivatives with significant inhibitory effect on the activity of urate transporter hURAT1, which comprises compound 48, a compound as represented by formula A in the present disclosure, with an $IC_{50}$ for the inhibition of the activity of the hURAT1 cells of 0.012 μmol, and it is expected that the compound can bring good clinical benefits to patients when it is administered at a lower dosage. The compound as represented by formula A obtained by the preparation method of compound 48 disclosed in CN106008340A was amorphous form when determined by XRPD. However, when the compound as represented by Formula A was obtained by using the above preparation method at an amplified level (for example, with a feed quantity of 27 g), it was found that there was always a chromatographic peak of an unknown impurity at a relative retention time (RRT) of about 0.62 for the compound as represented by formula A in the collected reversed-phase high-performance liquid chromatogram. It was difficult to remove this impurity completely or control it below the internal control standard (not to exceed 0.10%) by using purification methods such as slurrying or salting, which affects the quality and safety of the drug product. For this reason, the product was purified by recrystallization method to ensure that the purity of the drug meets the needs of the drug formulation and the clinical use.

It was also found that the amorphous form of the compound as represented by formula A suffers from strong hygroscopicity under condition of high humidity, which is very unfavorable for drug storage and solid formulation development.

Therefore, strict control of the limit of unknown impurities to improve the purity of the final product and preparation of a solid form with lower hygroscopicity for the compound as represented by formula A to meet the needs of final formulation and clinical use are urgent problems.

CONTENT OF THE DISCLOSURE

The problem to be solved in the present disclosure is to provide a crystal form of a fused ring derivative, a preparation method therefor and the use thereof in response to the defects such as insufficient purity and serious moisture absorption in the process of scaling up to produce compound as represented by formula A in the prior art. The crystal form in the present disclosure has high purity, good stability, and is non-hygroscopic; moreover, the solvent used for crystallization in the preparation method has the advantage of low residue and is suitable for industrialized production.

The present disclosure solves the above problems by the following technical solutions.

The present disclosure provides a crystal form I of the compound as represented by formula A has an X-ray Powder Diffraction pattern comprising diffraction peaks at angles 2θ of 8.3±0.2°, 12.8±0.2°, 13.4±0.2°, 17.5±0.2°, 17.9±0.2° and 23.3±0.2°, the X-ray Powder Diffraction is measured by Cu K-alpha radiation.

Further, the crystal form I of the compound as represented by formula A has an X-ray Powder Diffraction pattern comprising diffraction peaks at angles 2θ of 8.3±0.2°, 11.2±0.2°, 12.2±0.2°, 12.8±0.2°, 13.4±0.2°, 17.5±0.2°, 17.9±0.2°, 20.8±0.2°, 22.4±0.2° and 23.3±0.2°, the X-ray Powder Diffraction is measured by Cu K-alpha radiation.

Furthermore, the crystal form I of the compound as represented by formula A has an X-ray Powder Diffraction pattern comprising diffraction peaks at angles 2θ of 8.3±0.2°, 11.2±0.2°, 12.2±0.2°, 12.8±0.2°, 13.4±0.2°, 17.1±0.2°, 17.5±0.2°, 17.9±0.2°, 20.8±0.2°, 21.5±0.2°, 22.4±0.2°, 23.3±0.2°, 24.0±0.2°, 25.4±0.2°, 29.4±0.2° and 34.5±0.2°, the X-ray Powder Diffraction is measured by Cu K-alpha radiation.

In some embodiments of the present disclosure, the crystal form I of the compound as represented by formula A can also have an X-ray Powder Diffraction pattern measured by Cu K-alpha radiation, comprising diffraction peaks with data of diffraction angles 2θ, d-spacing and relative intensity of peak height shown in Table 3:

TABLE 3

| Number | 2θ(±0.2°) | d-spacing(Å) | Relative intensity of peak height (%) |
|---|---|---|---|
| 1 | 8.283 | 10.67 | 49.1 |
| 2 | 11.204 | 7.89 | 6.4 |
| 3 | 12.186 | 7.26 | 6.0 |
| 4 | 12.753 | 6.94 | 32.2 |
| 5 | 13.415 | 6.59 | 100.0 |
| 6 | 17.100 | 5.18 | 8.7 |
| 7 | 17.505 | 5.06 | 27.3 |
| 8 | 17.879 | 4.96 | 21.9 |
| 9 | 20.469 | 4.34 | 3.4 |
| 10 | 20.789 | 4.27 | 13.8 |
| 11 | 21.542 | 4.12 | 9.5 |
| 12 | 22.450 | 3.96 | 18.3 |
| 13 | 23.280 | 3.82 | 37.3 |
| 14 | 24.029 | 3.70 | 8.2 |
| 15 | 25.444 | 3.50 | 14.8 |
| 16 | 29.436 | 3.03 | 7.9 |
| 17 | 30.700 | 2.91 | 3.5 |
| 18 | 31.300 | 2.86 | 4.3 |
| 19 | 31.541 | 2.83 | 4.3 |
| 20 | 34.497 | 2.60 | 8.9 |

In some embodiments of the present disclosure, the crystal form I of the compound as represented by formula A, measured by Cu K-alpha radiation, has an X-ray Powder Diffraction pattern as shown in FIG. 2.

In some embodiments of the present disclosure, the crystal form I of the compound as represented by formula A has an infrared absorption spectrum (IR) comprising characteristic peaks at 3090 $cm^{-1}$, 3061 $cm^{-1}$, 2965 $cm^{-1}$, 2924 $cm^{-1}$, 2868 $cm^{-1}$, 2222 $cm^{-1}$, 1697 $cm^{-1}$, 1605 $cm^{-1}$, 1578 $cm^{-1}$, 1549 $cm^{-1}$, 1499 $cm^{-1}$, 1474 $cm^{-1}$, 1420 $cm^{-1}$, 1396 $cm^{-1}$, 1296 $cm^{-1}$, 1246 $cm^{-1}$, 1188 $cm^{-1}$, 1051 $cm^{-1}$ and 920 $cm^{-1}$.

In some embodiments of the present disclosure, the crystal form I of the compound as represented by formula A has an infrared absorption spectrum as shown in FIG. 3.

In some embodiments of the present disclosure, Differential Scanning Calorimetry (DSC) graph of the crystal form I of the compound as represented by formula A has an endothermic peak with onset temperature of 193±2 °C (for example, 192.79 °C) and peak temperature of 195±2 °C (for example, 194.58 °C).

In some embodiments of the present disclosure, the crystal form I of the compound as represented by formula A has a Differential Scanning Calorimetry (DSC) graph as shown in FIG. 4.

In some embodiments of the present disclosure, the crystal form I of the compound as represented by formula A has a Thermogravimetric Analysis (TGA) graph with no weight loss of volatiles when heated to 190 °C.

In some embodiments of the present disclosure, the crystal form I of the compound as represented by formula A has a Thermogravimetric Analysis (TGA) graph as shown in FIG. 5.

In some embodiments of the present disclosure, in the Dynamic Vapor Sorption (DVS) graph of the crystal form I of the compound as represented by formula A, the mass of crystal form I increases by 0.01% in the relative humidity from 0 to 95% compared with the initial mass.

In some embodiments of the present disclosure, the crystal form I of the compound as represented by formula A can have a Dynamic Vapor Sorption (DVS) graph as shown in FIG. 6.

In some embodiments of the present disclosure, the crystal form I of the compound as represented by formula A has a liquid nuclear magnetic hydrogen spectrum ($^1H$ NMR), in which the chemical shifts and integral values of the characteristic peaks were consistent with the structural formula of the compound as represented by formula A, and it is possible to confirm that the crystal form I is a non-solvated solid form of the compound as represented by formula A.

In some embodiments of the present disclosure, the crystal form I of the compound as represented by formula A has a water content of 0.05% determined by Karl Fischer's method, confirming that the crystal form I is a pure anhydrous solid.

The disclosure also provides a method of preparing the crystal form I of the compound as represented by formula A, which is solution 1 or solution 2;

solution 1: at 60-75 °C, cooling a mixture of the compound as represented by formula A, THF and anti-solvent, crystalizing and filtrating; the anti-solvent is methanol and/or water;

solution 2: at 60-70 °C, cooling a solution formed by a crystal form III and/or VI of the compound as represented by formula A and a solvent, precipitating and filtrating; the solvent is a mixed solvent of THF and isopropanol.

The compound as represented by formula A can be in any form, and can be obtained through any channel, in some embodiments, the compound as represented by formula A is prepared referring to CN106008340A.

In solution 1, amount of THF can be conventional in the art for performing such operations, provided that the compound as represented by formula A is dissolved, and in some embodiments, the volume-to-mass ration of the THF to the compound as represented by formula A is 3.0-30.0 mL/g, for example, 4.0 mL/g, 7.0 mL/g or 10.0 mL/g.

In solution 1, the mixture can be obtained by adding the compound as represented by formula A into a mixed solvent of THF and the anti-solvent, or by addition of the anti-solvent after the compound as represented by formula A was dissolved in THF.

In some embodiments, the volume ratio of THF to the anti-solvent is 0.5:1-5:1.

In some embodiments, when the anti-solvent is methanol, the volume ratio of THF to the anti-solvent is 0.5:1 to 2:1, for example, 1:1.

In some embodiments, when the anti-solvent is water, the volume ratio of THF to the anti-solvent is 0.5:1-5:1, for example, 1:1, 3.5:1, 4.4:1 or 5:1.

In solution 1, temperature of the cooling can be −20 to 20 °C, for example, −8 °C, 10 °C or 20 °C.

In solution 1, speed of the cooling can be 5-30 °C/h, for example, 10 °C/h or 20 °C/h.

In solution 1, the cooling also includes mixing the mixture with isopropanol, then cooling. For example, cooling the mixture to 20-8 °C, then adding isopropanol, and then performing filtration.

In solution 1, the filtrating can be conventional in the art for performing such operations, for example, filtrating under reduced pressure.

In solution 1, a post-treatment step of drying can be performed after the filtrating. Temperature and time of the drying can be determined conventionally by a skilled person in the art. For example, in some embodiments, the drying is performed at 65 °C under reduced pressure, the time of the drying can be 1 hour to 3 days.

In solution 2, temperature of the cooling can be −20 to 20 °C, for example, 5 °C.

In solution 2, speed of the cooling can be 5 to 30 °C/h, for example, 10 °C/h.

In solution 2, in the mixed solvent, volume ration of THF to isopropanol can be 0.5:1 to 2:1, for example, 1:1.

In solution 2, the filtrating can be conventional in the art for performing such operations, for example, filtrating under reduced pressure.

In solution 2, a post-treatment step of drying can be performed after the filtrating. Temperature and time of the drying can be determined conventionally by a skilled person in the art. For example, in some embodiments, the drying is performed at 65 °C under reduced pressure, the time of the drying can be 1 hour to 3 days.

In solution 2, the crystal form III of the compound as represented by formula A can be obtained by method comprising the following steps, removing the solvent from a solution of the compound as represented by formula A in THF. The removing can be performed by way of distillation (for example, distillation under reduced pressure).

In solution 2, in the method of preparation of the crystal form III of the compound as represented by formula A, the removing of the solvent may be preceded by filtrating the solution of the compound as represented by formula A in THF. The filtrating can be conventional in the art for performing such operations, for example, filtrating through a membrane, for another example, filtrating through a 0.45 μm nylon membrane.

The crystal form III of the compound as represented by formula A has an X-ray Powder Diffraction pattern comprising diffraction peaks at angles 2θ of 6.7±0.2°, 13.6±0.2°, 14.5±0.2°, 15.3±0.2°, 15.8±0.2°, 16.1±0.2°, 16.8±0.2°, 17.1±0.2°, 19.0±0.2°, 19.6±0.2°, 20.3±0.2° and 22.6±0.2°, the X-ray Powder Diffraction is measured by Cu K-alpha radiation.

Further, the crystal form III of the compound as represented by formula A, measured by Cu K-alpha radiation, has an X-ray Powder Diffraction pattern comprising diffraction peaks with data of diffraction angles 2θ, d-spacing and relative intensity of peak height as shown in Table 4:

TABLE 4

| Number | 2θ(±0.2°) | d-spacing(Å) | Relative intensity of peak height (%) |
|---|---|---|---|
| 1 | 6.729 | 13.13 | 100.0 |
| 2 | 13.601 | 6.51 | 39.9 |
| 3 | 14.527 | 6.09 | 11.3 |
| 4 | 15.280 | 5.79 | 5.3 |
| 5 | 15.653 | 5.66 | 3.4 |
| 6 | 15.832 | 5.59 | 5.4 |
| 7 | 16.133 | 5.49 | 2.7 |
| 8 | 16.822 | 5.27 | 3.4 |
| 9 | 17.138 | 5.17 | 8.1 |
| 10 | 17.317 | 5.12 | 5.9 |
| 11 | 18.954 | 4.68 | 11.9 |
| 12 | 19.646 | 4.52 | 13.3 |
| 13 | 20.323 | 4.37 | 33.2 |
| 14 | 20.798 | 4.27 | 4.0 |
| 15 | 22.371 | 3.97 | 5.1 |
| 16 | 22.632 | 3.93 | 6.0 |
| 17 | 23.149 | 3.84 | 3.7 |
| 18 | 24.727 | 3.60 | 3.2. |

Measured by Cu K-alpha radiation, the crystal form III of the compound as represented by formula A has an X-ray Powder Diffraction pattern as shown in FIG. 8.

The crystal form III of the compound as represented by formula A has a Differential Scanning Calorimetry (DSC) graph as shown in FIG. 9. DSC shows the crystal form III has an endothermic peak with onset temperature of 103±2 °C (for example, 103.39 °C) and peak temperature of 111±2 °C (for example, 111.33 °C); and an endothermic peak with onset temperature of 192±2 °C (for example, 191.85 °C) and peak temperature of 193±2 °C (for example, 193.04 °C).

The crystal form III of the compound as represented by formula A has a Thermogravimetric Analysis (TGA) graph as shown in FIG. 10. The TGA showed that the crystal form III loses 9.746% volatiles by weight when heated to about 190 °C, and the weight loss incurred above 190 °C is due to decomposition.

In solution 2, the crystal form VI of the compound as represented by formula A can be obtained by method of preparation comprising the following steps, cooling a solution of the compound as represented by formula A in 1,4-dioxane to −10 to −20 °C, filtrating, and drying.

In solution 2, in the method of preparing the crystal form VI of the compound as represented by formula A, temperature of the solution formed by the compound as represented by formula A with 1,4-dioxane is 40-120 °C, for example, 105±5 °C.

In solution 2, in the method of preparing the crystal form VI of the compound as represented by formula A, the cooling is fast cooling, for example, the solution was placed in a refrigerator at −10 to −20 °C immediately, the time for the placement may be from 1 to 3 days, for example, 3 days.

In solution 2, in the method of preparing the crystal form VI of the compound as represented by formula A, the filtrating can be conventional in the art for performing such operations, for example, filtrating under reduced pressure.

In solution 2, in the method of preparing the crystal form VI of the compound as represented by formula A, the drying can be performed under reduced pressure, for example, drying under reduced pressure at 60 °C.

The crystal form VI of the compound as represented by formula A has an X-ray Powder Diffraction pattern comprising diffraction peaks at angles 2θ of 6.3±0.2°. 12.7±0.2°, 14.1±0.2°, 14.6±0.2°, 17.3±0.2°, 17.8±0.2°, 19.1±0.2°, 19.5±0.2°, 22.4±0.2°, 24.6±0.2° and 25.2±0.2°, the X-ray Powder Diffraction is measured by Cu K-alpha radiation.

Preferably, the crystal form VI of the compound as represented by formula A, measured by Cu K-alpha radiation, can also have an X-ray Powder Diffraction pattern comprising diffraction peaks with data of diffraction angles 2θ, d-spacing and relative intensity of peak height as shown in Table 5:

TABLE 5

| Number | 2θ(±0.2°) | d-spacing(Å) | Relative intensity of peak height (%) |
|---|---|---|---|
| 1 | 6.299 | 14.02 | 100.0 |
| 2 | 12.742 | 6.94 | 25.8 |
| 3 | 14.143 | 6.26 | 2.3 |
| 4 | 14.599 | 6.06 | 3.7 |
| 5 | 15.470 | 5.72 | 2.0 |
| 6 | 16.555 | 5.35 | 1.6 |
| 7 | 17.284 | 5.13 | 7.1 |
| 8 | 17.836 | 4.97 | 4.3 |
| 9 | 18.180 | 4.88 | 1.0 |
| 10 | 19.121 | 4.64 | 8.8 |
| 11 | 19.538 | 4.54 | 12.4 |
| 12 | 21.249 | 4.18 | 1.4 |

TABLE 5-continued

| Number | 2θ(±0.2°) | d-spacing(Å) | Relative intensity of peak height (%) |
|---|---|---|---|
| 13 | 22.362 | 3.97 | 4.5 |
| 14 | 23.488 | 3.78 | 2.8 |
| 15 | 24.161 | 3.68 | 2.8 |
| 16 | 24.556 | 3.62 | 4.3 |
| 17 | 25.207 | 3.53 | 5.1 |
| 18 | 26.810 | 3.32 | 1.2 |
| 19 | 29.593 | 3.02 | 1.2. |

The crystal form VI of the compound as represented by formula A, measured by Cu K-alpha radiation, has an X-ray Powder Diffraction pattern as shown in FIG. 12.

The crystal form VI of the compound as represented by formula A has a Differential Scanning Calorimetry (DSC) graph as shown in FIG. 13. DSC shows the crystal form VI has an endothermic peak with onset temperature of 140±2 °C (for example, 140.47 °C) and peak temperature of 146±2 °C (for example, 145.60 °C), and, an endothermic peak with onset temperature of 192±2 °C (for example, 191.92 °C) and peak temperature of 193±2 °C (for example, 193.21 °C).

The crystal form VI of the compound as represented by formula A has a Thermogravimetric Analysis (TGA) graph as shown in FIG. 14. The TGA shows that the crystal form VI loses 11.545% volatiles by weight when heated to about 190 °C, and the weight loss incurred above 190 °C is due to decomposition.

The present disclosure also provides a crystal form IV of the compound as represented by formula A having an X-ray Powder Diffraction pattern comprising diffraction peaks at angles 2θ of 8.4±0.2°, 12.8±0.2°, 13.5±0.2°, 16.1±0.2°, 16.7±0.2°, 16.9±0.2°, 17.6±0.2°, 17.9±0.2°, 18.9±0.2°, 22.7±0.2°, 23.4±0.2°, 24.1±0.2° and 25.5±0.2°, the X-ray powder Diffraction is measured by Cu K-alpha radiation.

Preferably, the crystal form IV of the compound as represented by formula A, measured by Cu K-alpha radiation, has an X-ray Powder Diffraction pattern comprising diffraction peaks with data of diffraction angles 2θ, d-spacing and relative intensity of peak height as shown in Table 6:

TABLE 6

| Number | 2θ(°) | d-spacing(Å) | Relative intensity of peak height (%) |
|---|---|---|---|
| 1 | 8.391 | 10.53 | 61.8 |
| 2 | 12.293 | 7.19 | 6.9 |
| 3 | 12.848 | 6.88 | 18.0 |
| 4 | 13.508 | 6.55 | 100.0 |
| 5 | 14.647 | 6.04 | 6.5 |
| 6 | 16.119 | 5.49 | 6.3 |
| 7 | 16.682 | 5.31 | 36.2 |
| 8 | 16.945 | 5.23 | 27.4 |
| 9 | 17.153 | 5.17 | 20.0 |
| 10 | 17.605 | 5.03 | 48.5 |
| 11 | 17.968 | 4.93 | 14.5 |
| 12 | 18.920 | 4.69 | 24.3 |
| 13 | 20.141 | 4.41 | 8.3 |
| 14 | 20.595 | 4.31 | 13.7 |
| 15 | 20.880 | 4.25 | 11.7 |
| 16 | 21.639 | 4.10 | 14.2 |
| 17 | 22.728 | 3.91 | 18.8 |
| 18 | 23.354 | 3.81 | 24.6 |
| 19 | 24.112 | 3.69 | 14.9 |
| 20 | 24.737 | 3.60 | 8.6 |
| 21 | 25.535 | 3.49 | 30.8 |
| 22 | 29.538 | 3.02 | 14.5 |
| 23 | 34.593 | 2.59 | 10.0. |

The crystal form IV of the compound as represented by formula A, measured by Cu K-alpha radiation, has an X-ray Powder Diffraction pattern as shown in FIG. 16.

The crystal form IV of the compound as represented by formula A has a Differential Scanning Calorimetry (DSC) graph as shown in FIG. 17. DSC shows the crystal form IV has an endothermic peak with onset temperature of 191±2 °C (for example, 191.36 °C) and peak temperature of 194±2 °C (for example, 193.60 °C).

The crystal form IV of the compound as represented by formula A has a Thermogravimetric Analysis (TGA) graph as shown in FIG. 18. The TGA shows that the crystal form IV loses 0.364% volatiles by weight when heated to about 190 °C, and the weight loss incurred above 190 °C is due to decomposition.

The crystal form IV of the compound as represented by formula A has a water content of 0.3% determined by Karl Fischer's method, confirming that the crystal form IV-is a pure anhydrous solid form.

The crystal form IV of the compound as represented by formula A is obtained by a preparation method comprising the following steps: cooling a solution formed by the compound as represented by Formula A and 1,4-dioxane to room temperature, crystallizing, filtrating and drying.

In some embodiments, the temperature of the solution formed by the compound as represented by formula A and 1,4-dioxane was 40 to 120 °C, for example, 80 °C.

The solution may be a saturated solution, and the saturated solution is treated by filtrating, for example, filtrating with a 0.45 μm nylon filter membrane while still hot, to obtain a saturated solution.

In some embodiments, the cooling was slow, and rate of the cooling may be 5 °C/h.

In some embodiments, temperature of the crystallizing is room temperature.

The filtrating may be a conventional operation in the art for performing such filtrating, for example, filtrating under reduced pressure.

The drying may be performed under reduced pressure, for example, drying under reduced pressure at 40 °C.

The present disclosure provides an application of the crystal form I of a compound as represented by formula A, as described above, in the preparation of a drug for the prevention and/or treatment of hyperuricemia or its related disease.

Wherein, the related disease of hyperuricemia such as one or more selected from gout, hypertension, diabetes, hypertriglyceridemia, metabolic syndrome, coronary heart disease and kidney damage.

The present disclosure provides a method for prevention and/or treatment of hyperuricemia or its related disease, including administrating an effective amount of the crystal form I of the compound as represented by formula A as described above to the subject. Wherein, the hyperuricemia or its related disease such as one or more selected from gout, hypertension, diabetes, hypertriglyceridemia, metabolic syndrome, coronary heart disease and kidney damage.

The present disclosure also provides an application of the crystal form I of the compound as represented by formula A as described above in the preparation of a uric acid transporter 1 inhibitor.

The present disclosure provides a method for inhibiting uric acid transporter 1, including administrating an effective amount of the crystal form I of the compound as represented by formula A as described above to the subject.

In some embodiments of the present disclosure, the uric acid transporter 1 inhibitor may be used in mammalian organisms; alternatively, used in vitro, primarily for experimental purposes, for example, as a standard or control sample to provide a comparison, or as a kit according to conventional methods in the field, to provide a rapid assay of the effect of uric acid transporter 1 inhibition.

The present disclosure also provides a pharmaceutical composition comprising a therapeutically effective amount of the crystal form I of the compound as represented by formula A as described above, and one or more pharmaceutically acceptable carriers and/or diluents thereof.

The present disclosure also provides a pharmaceutical composition comprising a therapeutically effective amount of the crystal form I of the compound as represented by formula A as described above and other uric acid-lowering drugs.

Wherein the other uric acid-lowering drug is one or more of a uric acid transporter 1 inhibitor, a xanthine oxidase inhibitor, a xanthine oxidoreductase and a xanthine dehydrogenase inhibitor.

In some embodiments of the present disclosure, the other uric acid-lowering drug is allopurinol and/or Febuxostat.

In the present disclosure, there is no particular limitation on the method of administration of the described pharmaceutical compositions, which may be administered in a variety of dosage forms of choice, depending on the patient's age, sex, and other conditions and symptoms, for example, tablets, pills, solutions, suspensions, emulsions, granules, or capsules are administered orally; injections may be administered alone or mixed with injectable delivery solutions (e.g., dextrose solutions and amino acid solutions) for intravenous injection; and suppositories are for administering drug to the rectum.

In some examples, the crystal form I of the compound as represented by formula A will not be transformed when formulated with one or more pharmaceutically acceptable carriers and/or excipients and/or diluents.

In some examples, the crystal form I of the compound as represented by formula A will not be transformed when formed into a pharmaceutical composition with other uric acid-lowering drugs.

On the basis of not violating the common knowledge in the field, each of the above preferred conditions, can be arbitrarily combined to obtain each of the preferred examples of the present disclosure.

In the present disclosure, compound 48-a is synthesized by reference to CN106008340A, and all other reagents and raw materials used are commercially available.

In the present disclosure, the ratio of solvents is by volume, if not otherwise specified.

The positive and progressive effect of the present disclosure is that the crystal form I of the compound as represented by formula A provided by the present disclosure has high purity, which could meet the needs of formulation preparation and clinical use, possesses good stability, non-hygroscopic, and is not easy to occur polymorphic transition; and the method of preparation is simple, and the crystallization solvents used are low-residue, which is suitable for industrialized production.

DETAILED DESCRIPTION OF THE EMBODIMENT

Figure 1:
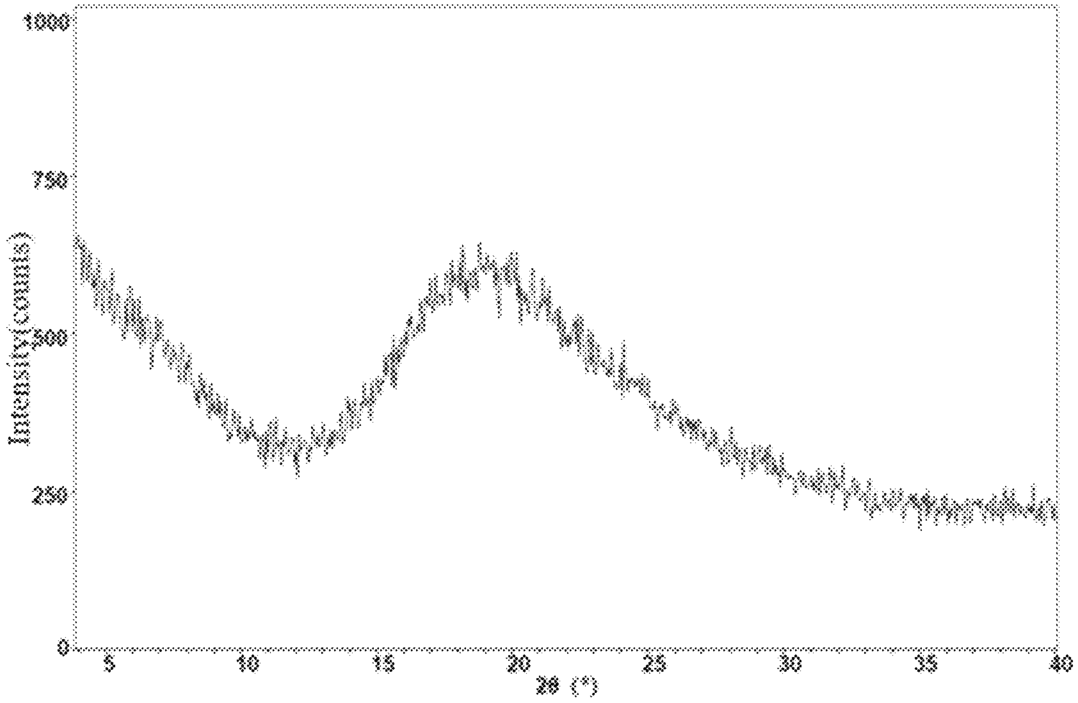
FIG. 1 is the X-ray Powder Diffraction pattern of the amorphous form of the compound as represented by formula A obtained based on the method in patent CN106008340A.

The present disclosure is further described below by way of embodiments, but the disclosure is not thereby limited to the described embodiments. Experimental methods for which specific conditions are not indicated in the following embodiments are selected according to conventional methods and conditions, or according to the products' description. The solvents involved in the following embodiment are all analytical or chromatographic pure, and when the solvent is a mixed solvent, the ration is a volume ratio unless otherwise specified.

The test instruments and test conditions used for the experiments in this disclosure:

(1) X-ray Powder Diffraction (X-Ray Powder Diffraction, XRPD)

Bruker's D8 Advance X-ray powder diffractometer and K-alpha spectrum of Cu target (λ=1.5406 Å) were used to test, with a voltage of 40 kV, a current of 40 mA, a scanning angle range of 4°-40°, a step size of 0.02°, and a scanning speed of 8°/min.

(2) Infrared Absorption Spectroscopy, IR

According to the infrared spectrophotometric method in the four parts general principles 0402 of the Chinese Pharmacopoeia 2020 edition, the test sample was prepared by the potassium bromide pressed tablets method, and the IR absorption spectra were collected in the wave number range of 4000-400 $cm^{-1}$. The number of scans for the test sample was 45, and the resolution of the instrument was 4 $cm^{-1}$, detected by the Shimadzu Presitage 21 Fourier Transform Infrared (FTIR) spectrometer.

(3) Differential Scanning Calorimeter (DSC)

A Q2000 or DSC25 type differential scanning calorimeter from TA Instruments was used, the atmosphere was nitrogen, the temperature rate was 10 °C/min, and the temperature range was 25-300 °C.

(4) Thermo Gravimetric Analysis (TGA)

A Q500 thermogravimetric analyzer from TA Instruments was used to heat with a range of 25-300 °C—at a heating rate of 10 °C/min at an atmosphere of nitrogen.

(5) Dynamic Vapor Sorption (DVS)

An Advantage 1.0 dynamic moisture adsorption instrument from SMS was used to detect, the temperature is 25 °C, the relative humidity range is 0%-95%, humidity change step is relative humidity 5%, when the value of the mass change rate dm/dt is less than 0.002%, it is considered equilibrium of the balance, when the mass change rate is less than 0.01%/minute within 5 minutes, it is considered as standards of equilibrium in detection process, the maximum equilibrium time is 2 hours.

(6) Proton Nuclear Magnetic Resonance ($^1$H NMR)

Liquid nuclear magnetic hydrogen spectrum was collected on a Bruker 400 MHz NMR spectrometer and the samples were dissolved in dimethyl sulfoxide-d6.

Example 1

Synthesis of the Compound as Represented by Formula A

The following is synthetic route of the compound as represented by formula A:

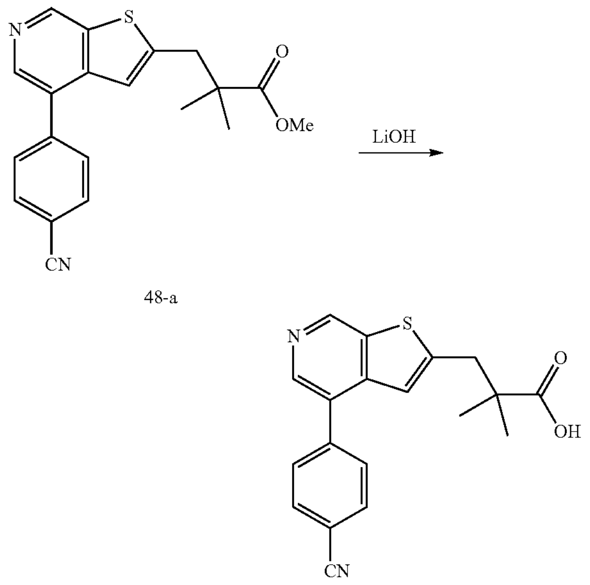

48-a

48

According to the method of synthesizing compound 48 in Chinese patent CN106008340A, under room temperature condition, 27 g of compound 48-a (methyl 3-[4-(4-cyanophenyl)thieno[2,3-c]pyridin-2-yl]-2,2-dimethylpropanoate) (76 mmol) was added into a mixed solution of methanol (200 mL), tetrahydrofuran (1.0 L) and water (200 mL), followed by addition of 13 g of lithium hydroxide (308 mmol). The resulting mixture was stirred for 6 hours, adjusted to pH=5-6 by adding 1M aqueous hydrochloric acid, and concentrated under reduced pressure. The residue was adjusted to pH=7-8 with 2M aqueous sodium hydroxide and extracted with ethyl acetate (2L) to remove impurities. The aqueous phase was adjusted to pH=5-6 with 1M aqueous hydrochloric acid and extracted with ethyl acetate (3L×2). The organic phases were combined, dried over anhydrous sodium sulfate and filtered at reduced pressure. The filtrate was distilled at reduced pressure to give 20 g yellow solid.

LC-MS (ESI): m/z=337 $[M+H]^+$.

$^1$H NMR (400 MHz, DMSO-$_{d6}$) δ 12.58 (s, 1H), 9.21 (s, 1H), 8.49 (s, 1H), 8.03 (d, 2H, J=8.4 Hz), 7.84 (d, 2H, J=8.4 Hz), 7.30 (s, 1H), 3.22 (s, 2H), 1.17 (s, 6H).

Determined by $^1$H NMR and LC-MS (ESI), the resulting yellow solid was confirmed to be compound 48, that is, the compound as represented by formula A as described in the present invention. Took appropriate amount of the sample for the XRPD test, which was shown to be in amorphous form and the XRPD pattern is shown in FIG. 1.

The sample was prepared with acetonitrile/water/trifluoroacetic acid (300/700/2) to a final concentration of 1 mg/mL, and analyzed by reversed-phase HPLC on a Waters SunFire column (3.5 μm, 4.6*150 mm) in the following chromatographic conditions: 0.1% trifluoroacetic acid-water solution was used as the mobile phase A, and 0.1% trifluoroacetic acid-acetonitrile solution was used as the mobile phase B, and the mobile phase B increased from 15% to 23% within 14 min, followed by 23% to 32% within 16 min, then from 32% to 80% within 15 min and held for 5 min, and finally from 80% back to 15% within 0.01 min and held for 10 min; the column temperature was 30 °C; the injection volume was 10 μL; the detection wavelength was 246 nm. The purity of the compound as represented by formula A in the sample was 98.6% by area normalization method, and the content of an unknown impurity was 0.17% relative to the retention time (RRT) of the compound as represented by formula A at about 0.62 in the high performance liquid chromatogram, which exceeded the internal control standard (not to exceed 0.10%). The compound as represented by formula A obtained by the preparation of Example 1 was used as a starting material for the following Examples 2 to 8.

Example 2

Purification of the Compound as Represented by Formula A by Extraction

The compound as represented by formula A was purified separately according to the operating method described below, and the experimental results are shown in Table 1 below.

Three portions of the compound as represented by formula A, each 0.5 g, were each added with 5 mL of water, and the solids were all dissolved by adjusting to pH=11 with 10% sodium carbonate solution or 2M lithium hydroxide solution, and then extracted with 2-methyltetrahydrofuran, dichloromethane, or toluene (5 mL×2) to remove impurities, respectively. The aqueous phase was adjusted to pH=3-4 with 1M aqueous hydrochloric acid, filtered and dried.

The purity of the product was analyzed by reversed-phase HPLC and the crystal form of the product was determined by XRPD.

TABLE 1

| Amount | Solution used to adjust pH | Solvent and volume | Crystal form | Purity of the product | Content of unknown impurity with RRT of about 0.62 in the product |
|---|---|---|---|---|---|
| 0.5 g | 10% sodium carbonate solution | 2-methyltetrahydrofuran, 10 mL | amorphous | 99.1% | 0.13% |
| 0.5 g | 10% sodium carbonate solution | toluene, 10 mL | amorphous | 99.0% | 0.15% |
| 0.5 g | 2M LiOH solution | dichloromethane, 10 mL | amorphous | 99.1% | 0.12% |

The above results show that the organic solvent extraction has a certain effect on the removal of the unknown impurity with an RRT of about 0.62, but fails to strictly control this impurity below the internal control standard (not to exceed 0.10%).

Example 3

Purification of the Compound as Represented by Formula A by Slurrying

The effect of slurrying with different solvents on the purification of the compound as represented by formula A was investigated according to the operation method described below, and the experimental results are shown in Table 2 below.

Three portions of the compound as represented by formula A, each 0.1 g, were added with appropriate volume of a single solvent or a mixture of solvents, slurried for 4 hours at room temperature, filtered and dried.

The purity of the products was analyzed by reversed phase HPLC and the crystal form of the products was determined by XRPD.

TABLE 2

| Solvent for slurrying | Crystal form | Purity of the product | Content of unknown impurity with RRT of about 0.62 in the product |
|---|---|---|---|
| ethanol | amorphous | 99.2% | 0.17% |
| THF/water (5/1) | amorphous | 99.3% | 0.12% |
| THF/isopropanol (7/30) | amorphous | 99.3% | 0.12% |

The results above show by slurrying fails to strictly control the unknown impurity with RRT of about 0.62 in the product below the internal control standard (not to exceed 0.10%).

Example 4

Preparation of Crystal Form I of the Compound as Represented by Formula A

A hot and clear solution was obtained by stirring and refluxing 5.0 g of the compound as represented by formula A in a mixed solvent of 35 mL of tetrahydrofuran and 7 mL of water at 70-75 °C, the temperature was slowly reduced to about 10 °C at a rate of 10 °C/hour, and the precipitated solid was filtered out, and dried under reduced pressure at 65 °C overnight to give 2.2 g of a white solid at a yield of 44.5%.

The solid was analyzed by reversed phase HPLC, purity of the compound as represented by formula A was 99.6%, and content of the unknown impurity with an RRT of about 0.62 was 0.05%.

Figure 2:
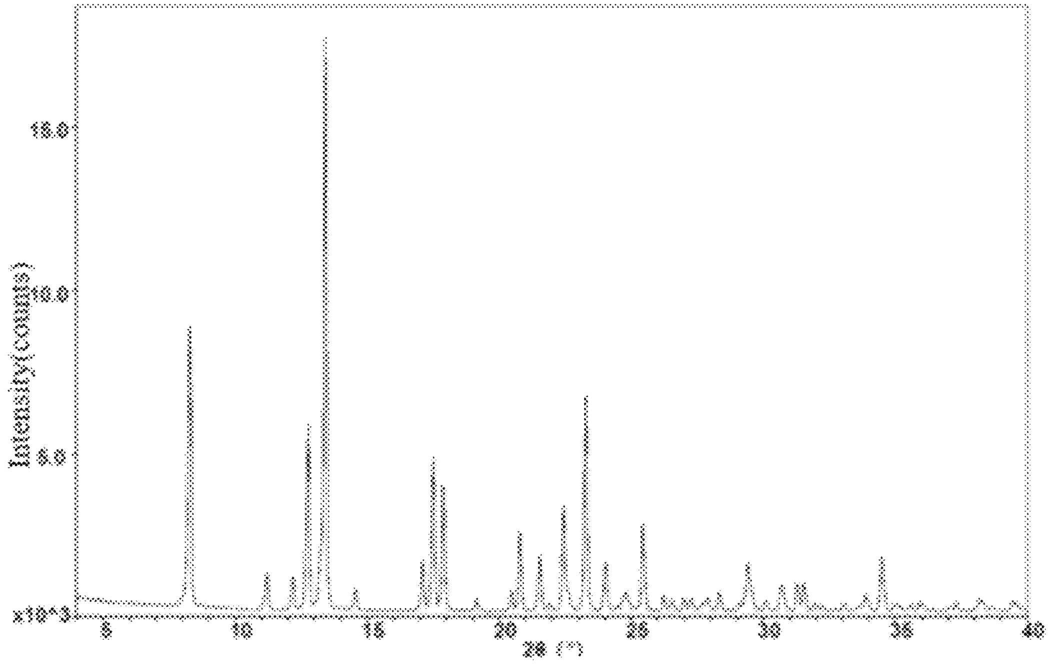
FIG. 2 is the X-ray Powder Diffraction pattern of the crystal form I of the compound as represented by formula A.

The solid obtained was crystal form I of the compound as represented by formula A, whose X-ray Powder Diffraction pattern was shown in FIG. 2. The 2θ angle, d-spacing, and peak height relative intensity data of the major diffraction peaks of the solid in the X-ray Powder Diffraction pattern expressed in terms of the 2θ angle are shown in Table 3 below:

TABLE 3

| number | 2θ (±0.2°) | d-spacing (Å) | Relative height of the peak (%) |
|---|---|---|---|
| 1 | 8.283 | 10.67 | 49.1 |
| 2 | 11.204 | 7.89 | 6.4 |
| 3 | 12.186 | 7.26 | 6.0 |
| 4 | 12.753 | 6.94 | 32.2 |
| 5 | 13.415 | 6.59 | 100.0 |
| 6 | 17.100 | 5.18 | 8.7 |
| 7 | 17.505 | 5.06 | 27.3 |
| 8 | 17.879 | 4.96 | 21.9 |
| 9 | 20.469 | 4.34 | 3.4 |
| 10 | 20.789 | 4.27 | 13.8 |
| 11 | 21.542 | 4.12 | 9.5 |
| 12 | 22.450 | 3.96 | 18.3 |
| 13 | 23.280 | 3.82 | 37.3 |
| 14 | 24.029 | 3.70 | 8.2 |
| 15 | 25.444 | 3.50 | 14.8 |
| 16 | 29.436 | 3.03 | 7.9 |
| 17 | 30.700 | 2.91 | 3.5 |
| 18 | 31.300 | 2.86 | 4.3 |
| 19 | 31.541 | 2.83 | 4.3 |
| 20 | 34.497 | 2.60 | 8.9. |

Figure 3:
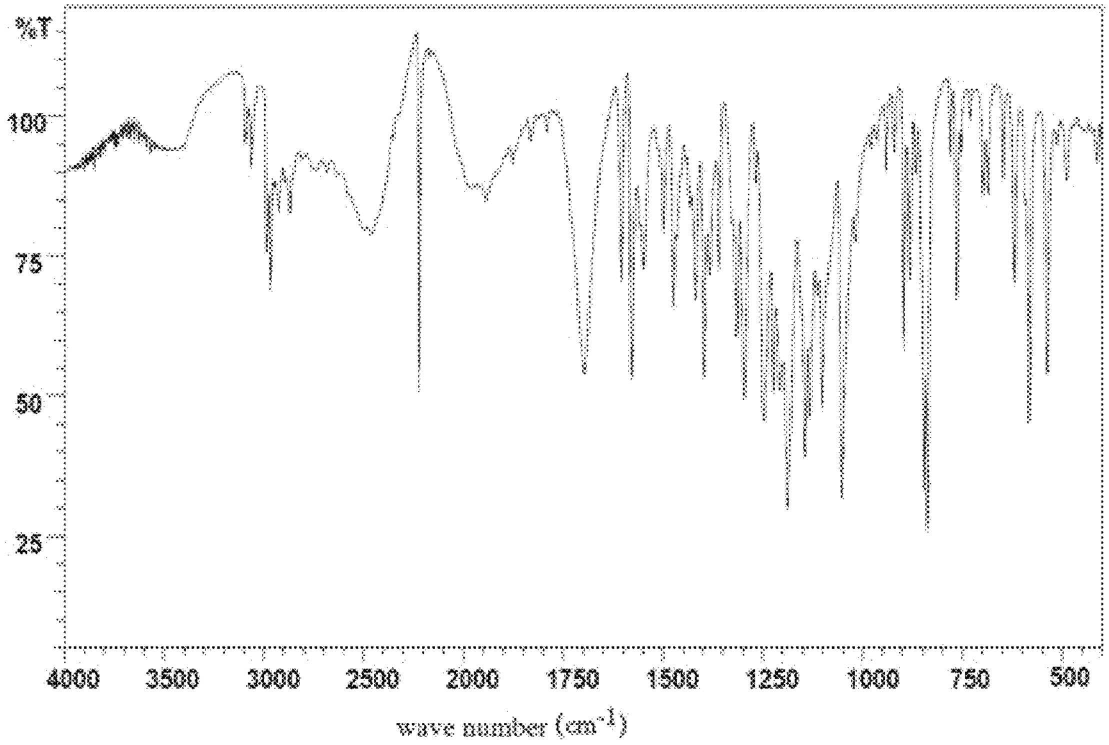
FIG. 3 is the infrared absorption spectra of the crystal form I of the compound as represented by formula A.

The crystal form I of the compound as represented by formula A has an infrared absorption spectrum as shown in FIG. 3, which has an infrared absorption peaks at 3090 $cm^{-1}$, 3061 $cm^{-1}$, 2965 $cm^{-1}$, 2924 $cm^{-1}$, 2868 $cm^{-1}$, 2222 $cm^{-1}$, 1697 $cm^{-1}$, 1605 $cm^{-1}$, 1578 $cm^{-1}$, 1549 $cm^{-1}$, 1499 $cm^{-1}$, 1474 $cm^{-1}$, 1420 $cm^{-1}$, 1396 $cm^{-1}$, 1296 $cm^{-1}$, 1246 $cm^{-1}$, 1188 $cm^{-1}$, 1051 $cm^{-1}$ and 920 $cm^{-1}$.

Figure 4:
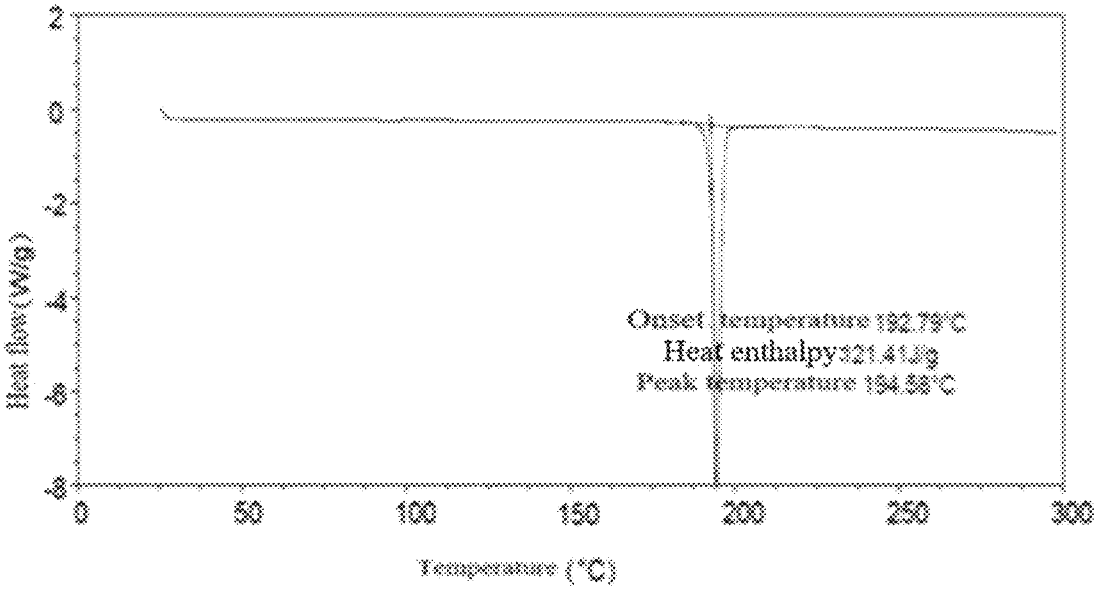
FIG. 4 is the Differential Scanning Calorimetry diagram of the crystal form I of compound as represented by formula A.

The crystal form I has a DSC graph as shown in FIG. 4, which has an endothermic peak with onset temperature of 192.79 °C and peak temperature of 194.58 °C.

Figure 5:
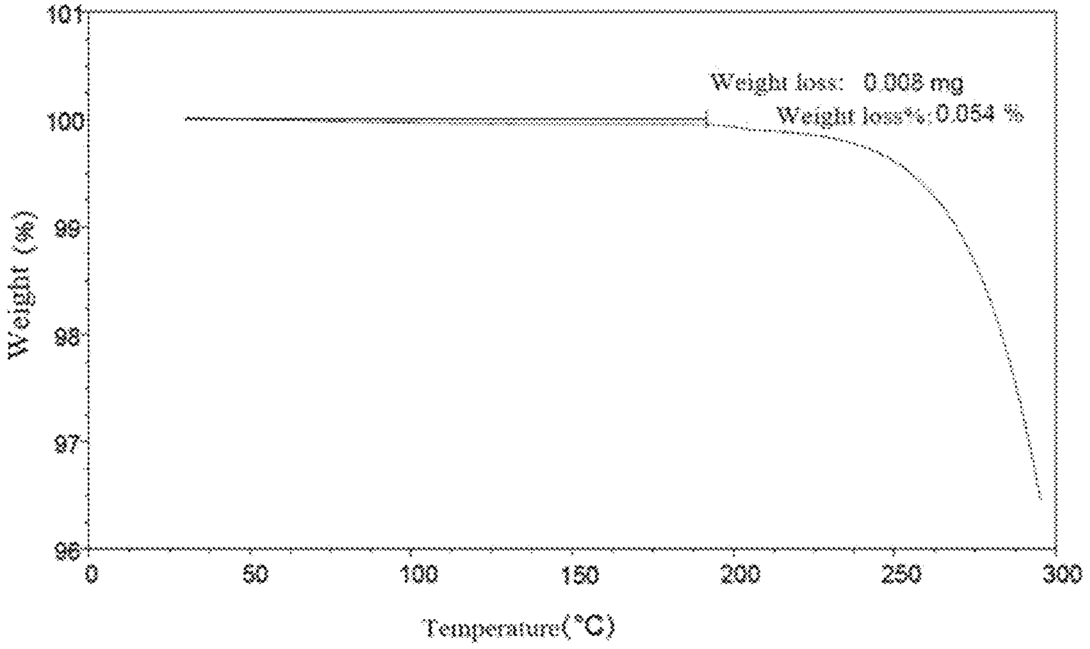
FIG. 5 is the Thermogravimetric Analysis plot of the crystal form I of the compound as represented by formula A.

TGA shows the crystal form I has 0.054% weight loss of volatiles when heated to 190 °C, and the weight loss incurred above 190 °C is due to decomposition, the TGA graph is shown as FIG. 5.

Figure 6:
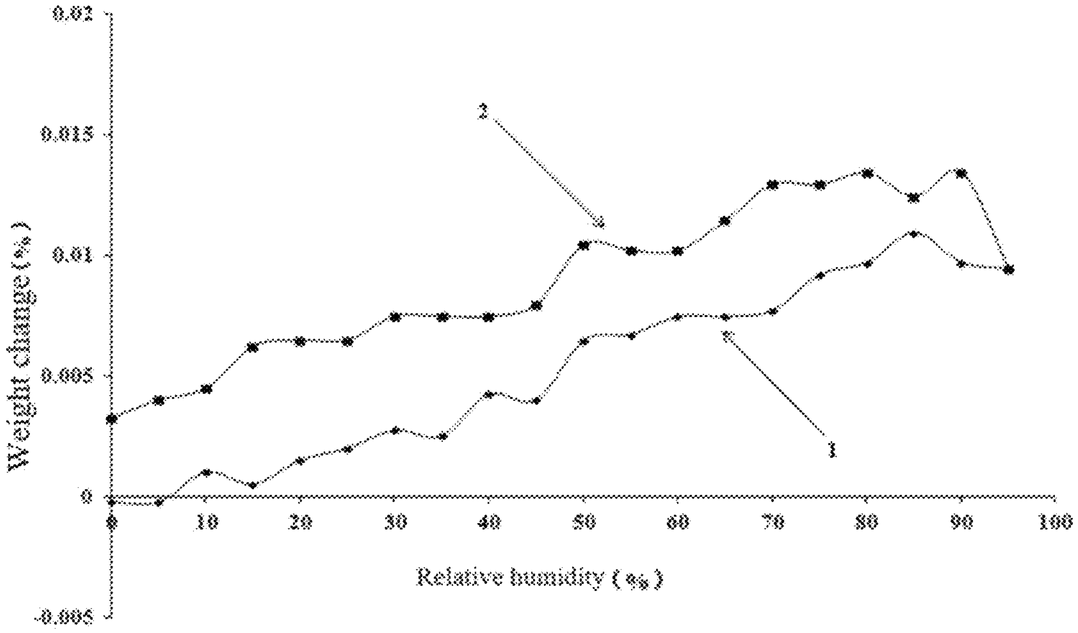
FIG. 6 is the Dynamic Vapor Sorption plot of the crystal form I of the compound as represented by formula A; wherein 1 is the sorption curve and 2 is the desorption curve.

DVS shows the crystal form I increases by 0.00944% mass from RH0 to RH95% compared to the initial mass, and the DVS graph is shown as FIG. 6.

Figure 7:
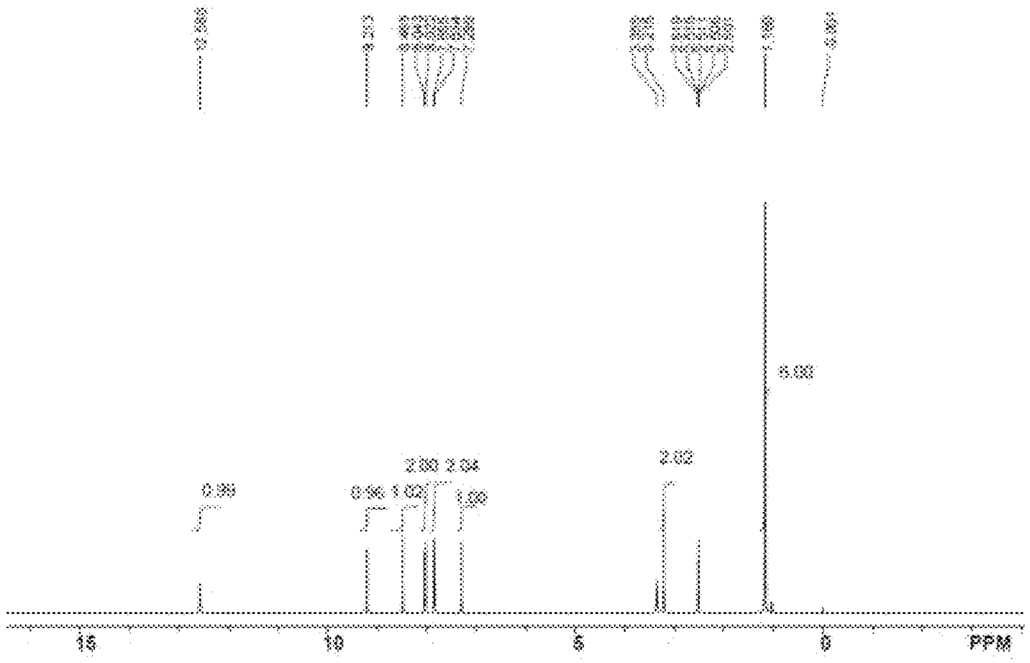
FIG. 7 is the liquid nuclear magnetic hydrogen spectrum of the crystal form I of the compound as represented by formula A.

The chemical shifts and integral values of the characteristic peaks of the crystal form I obtained by $^1H$ NMR test were consistent with the structural formula of the compound as represented by formula A. No characteristic peaks of the residual solvent used in crystallization was observed, and the $^1H$ NMR spectrum of crystal form I is shown in FIG. 7.

The water content in the crystal form I was 0.05% as determined by Karl Fischer's method, confirming that the crystal form I is an anhydrous solid form of the compound as represented by formula A.

According to the residual solvent determination method (Chinese Pharmacopoeia 2020 edition <0861>), analyzed by gas chromatography (GC), the residual solvent in the crystal form I was in accordance with the specified limit (tetrahydrofuran should not exceed 0.072%).

Example 5

Preparation of Crystal Form I of the Compound as Represented by Formula A

A hot and clear solution was obtained by stirring and refluxing 0.3 g of the compound as represented by formula A in a mixed solvent of 1.2 mL of tetrahydrofuran and 1.2 mL of methanol at about 60 °C, the temperature was slowly reduced to about 20 °C at a rate of 10 °C/hour, and the precipitated solid was filtered out, and dried under reduced pressure at 65 °C overnight to give 0.21 g of a white solid at a yield of 70.0%. After investigated and compared, X-ray Powder Diffraction pattern of this sample was determined to be the crystal form I. Analyzed by reversed phase HPLC, the purity of the compound as represented by formula A in the sample was 99.5%, and the content of the unknown impurity with RRT of about 0.62 was 0.09%. According to the residual solvent determination method (Chinese Pharmacopoeia 2020 edition <0861>), analyzed by GC, the residual solvents in this sample were in accordance with the specified limits (tetrahydrofuran should not exceed 0.072% and methanol should not exceed 0.3%).

Example 6

Preparation of the Crystal Form I of the Compound as Represented by Formula A 0.5 g of the compound as represented by formula A was mixed in 5 mL of a mixture of tetrahydrofuran/water (7/1.6, V/V)—at 65±5 °C The resulting mixture was stirred at this temperature for 24 hours, then cooled down to about 10 °C at a rate of 30 °C/hour. The precipitated solid was filtered out, and dried under reduced pressure at 65 °C overnight to give 0.37 g of a white solid at a yield of 74.0%. After investigated and compared, X-ray Powder Diffraction pattern of this sample was determined to be the crystal form I. Analyzed by reversed phase HPLC, purity of the compound as represented by formula A in this sample was 99.8%, and content of the unknown impurity with RRT of about 0.62 was 0.02%. According to the residual solvent determination method (Chinese Pharmacopoeia 2020 edition <0861>), the residual solvent in this sample was analyzed by GC, and the residual solvent in this sample was in accordance with the specified limit (tetrahydrofuran should not exceed 0.072%).

Example 7

Preparation of the Crystal Form I of the Compound as Represented by Formula A 1.0 g of the compound as represented by formula A in 10 mL of tetrahydrofuran was refluxed at 65-70 °C, stirred to obtain a hot and clear solution. 10 mL of water was slowly added by dropwise into the above solution, the temperature was slowly reduced to about 10 °C at a rate of 10 °C/hour and kept stirring overnight, and the precipitated solid was filtered out, and dried under reduced pressure at 65 °C overnight to give 0.65 g of a white solid at a yield of 65.0%. After investigated and compared, X-ray Powder Diffraction pattern of this sample was determined to be the crystal form I. Analyzed by reversed phase HPLC, purity of the compound as represented by formula A in this sample was 99.8%, and content of the unknown impurity with RRT of about 0.62 was 0.02%. According to the residual solvent determination method (Chinese Pharmacopoeia 2020 edition <0861>), the residual solvent in this sample was analyzed by GC, and the residual solvent was in accordance with the specified limit (tetrahydrofuran should not exceed 0.072%).

Example 8

Preparation of the Crystal Form I of the Compound as Represented by Formula A

A hot and clear solution was obtained by stirring and refluxing 1.0 g of the compound as represented by formula A in a mixed solvent of 7 mL of tetrahydrofuran and 2 mL of water at 70-75 °C. The solution was slowly reduced to about 20 °C at a rate of 10 °C/hour, was added 5 mL of isopropanol and the temperature was slowly reduced to about −8 °C at a rate of 10 °C/hour, stirred for 5 hours, and the precipitated solid was filtered out, and dried under reduced pressure at 65 °C overnight to obtain 0.76 g of white solid at a yield of 76.0%. After investigated and compared, X-ray Powder Diffraction pattern of this sample was determined to be the crystal form I. Analyzed by reversed phase HPLC, purity of the compound as represented by formula A in this sample was 99.9%, and content of the unknown impurity with RRT of about 0.62 was 0.02%. According to the residual solvent determination method (Chinese Pharmacopoeia 2020 edition <0861>), analyzed by GC, there was no residual tetrahydrofuran in this sample, and the content of isopropanol was 0.18%, and the residual solvents were in accordance with the specified limits (tetrahydrofuran should not exceed 0.072%, and isopropanol should not exceed 0.5%).

Example 9

Preparation of the Crystal Form I of the Compound as Represented by Formula A

A hot and clear solution was obtained by stirring 0.1 g of the compound as represented by formula A (crystal form III) in a mixed solvent of 0.5 mL of tetrahydrofuran and 0.5 mL of isopropanol at 60-70 °C, the temperature was slowly reduced to about 5 °C at a rate of 10 °C/hour, and the precipitated solid was filtered out and dried under reduced pressure at 65 °C overnight. After investigated and compared, X-ray Powder Diffraction pattern of this sample was determined to be the crystal form I.

Analyzed by reversed phase HPLC, purity of the compound as represented by formula A in this sample was 99.8%, and content of the unknown impurity with RRT of about 0.62 was 0.07%.

Example 10

Preparation of the Crystal Form I of the Compound as Represented by Formula A A hot and clear solution was obtained by stirring 0.1 g of the compound as represented by formula A (crystal form VI) in a mixed solvent of 0.5 mL of tetrahydrofuran and 0.5 mL of isopropanol at 60-70 °C, the temperature was slowly reduced to about 5 °C at a rate of 10 °C/hour, and the precipitated solid was filtered out and dried under reduced pressure at 65 °C overnight. After investigated and compared, X-ray Powder Diffraction pattern of this sample was determined to be the crystal form I.

Analyzed by reversed phase HPLC, purity of the compound as represented by formula A in this sample was 99.8% and content of the unknown impurity with an RRT of about 0.62 was 0.05%.

Example 11

Preparation of the Crystal Form I of the Compound as Represented by Formula A A batch of crude product of the compound as represented by formula A was synthesized again according to the method of Example 1, and the purity of the compound as represented by formula A in this crude product was 99.1% and content of the unknown impurity with RRT of about 0.62 was 0.15% by using reversed phase HPLC analysis. A hot and clear solution was obtained by stirring and refluxing 50 g of the crude product in a mixed solvent of 350 mL of tetrahydrofuran and 100 mL of water at 70-75 °C, then the temperature was slowly reduced to about 20 °C at a rate of 10 °C/hour. The above solution was added with 250 mL of isopropanol and the temperature was slowly reduced to about −8 °C at a rate of 10 °C/hour, stirred for 5 hours. Precipitated solid was filtered out and dried under reduced pressure at 65 °C overnight to give 41.0 g of white solid at a yield of 82.0%. After investigated and compared, X-ray Powder Diffraction pattern of this sample was determined to be the crystal form I. Analyzed by reversed phase HPLC, purity of the compound as represented by formula A in this sample was 99.9% and content of the unknown impurity with an RRT of about 0.62 was 0.01%. According to the residual solvent determination method (Chinese Pharmacopoeia 2020 edition <0861>), no tetrahydrofuran residue was detected in this sample by GC, and content of isopropanol was 0.073%, and the residual solvents were in accordance with the specified limits (tetrahydrofuran should not exceed 0.072%, and isopropanol should not exceed 0.5%).

Example 12

Preparation of the Crystal Form III of the Compound as Represented by Formula A At room temperature, 0.75 g of the crude product of the compound as represented by formula A prepared in Example 11 was mixed in 50 mL of tetrahydrofuran. The resulting mixture was sonicated until the solid was nearly dissolved, filtered it through 0.45 μm nylon filter membrane, and then the filtrate was distilled at room temperature under reduced pressure to remove the solvent, obtaining 0.70 g of a white solid at a yield of 93.2%.

Figure 8:
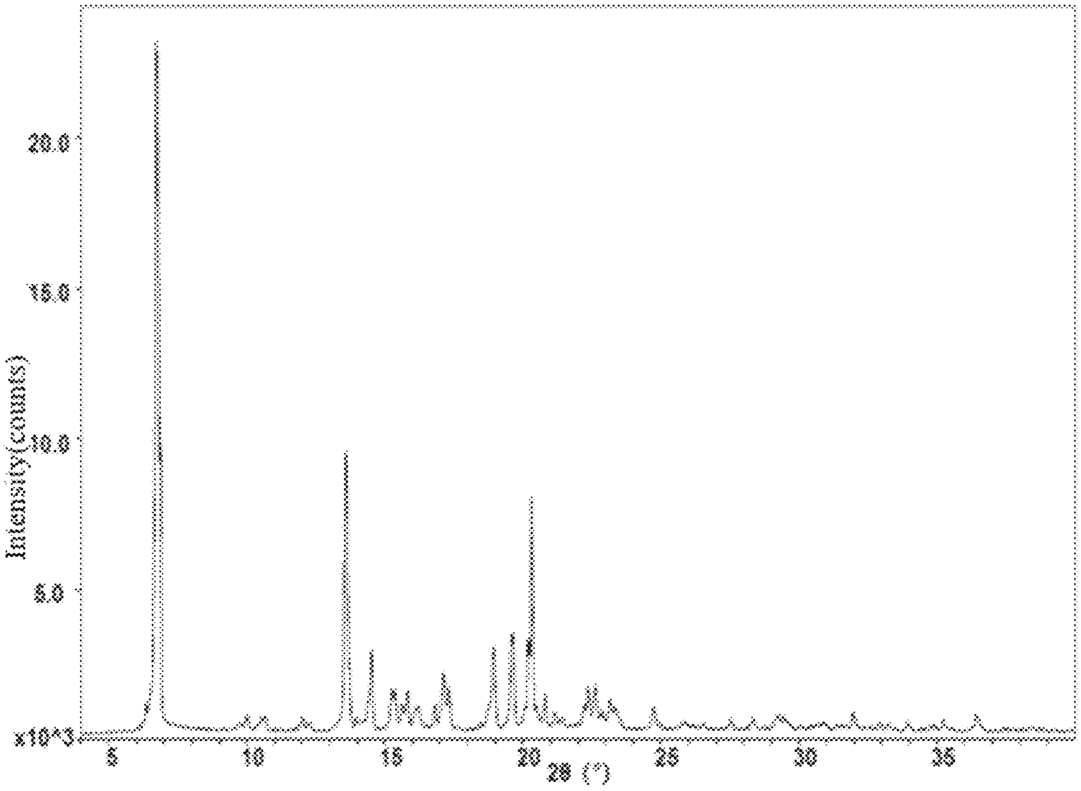
FIG. 8 is the X-ray Powder Diffraction pattern of the crystal form III of the compound as represented by formula A.

The resulting solid was the crystal form III of the compound as represented by formula A, whose X-ray Powder Diffraction pattern was shown in FIG. 8, and data of the major diffraction peaks of the solid about 2θ angle, d-spacing, and relative intensity of peak height in the X-ray Powder Diffraction pattern expressed in terms of the 2θ angle was shown in Table 4 below:

TABLE 4

| Number | 2θ (°) | d-spacing (Å) | relative intensity of peak height (%) |
|---|---|---|---|
| 1 | 6.729 | 13.13 | 100.0 |
| 2 | 13.601 | 6.51 | 39.9 |
| 3 | 14.527 | 6.09 | 11.3 |
| 4 | 15.280 | 5.79 | 5.3 |
| 5 | 15.653 | 5.66 | 3.4 |
| 6 | 15.832 | 5.59 | 5.4 |
| 7 | 16.133 | 5.49 | 2.7 |
| 8 | 16.822 | 5.27 | 3.4 |
| 9 | 17.138 | 5.17 | 8.1 |
| 10 | 17.317 | 5.12 | 5.9 |
| 11 | 18.954 | 4.68 | 11.9 |
| 12 | 19.646 | 4.52 | 13.3 |
| 13 | 20.323 | 4.37 | 33.2 |
| 14 | 20.798 | 4.27 | 4.0 |
| 15 | 22.371 | 3.97 | 5.1 |
| 16 | 22.632 | 3.93 | 6.0 |
| 17 | 23.149 | 3.84 | 3.7 |
| 18 | 24.727 | 3.60 | 3.2. |

Figure 9:
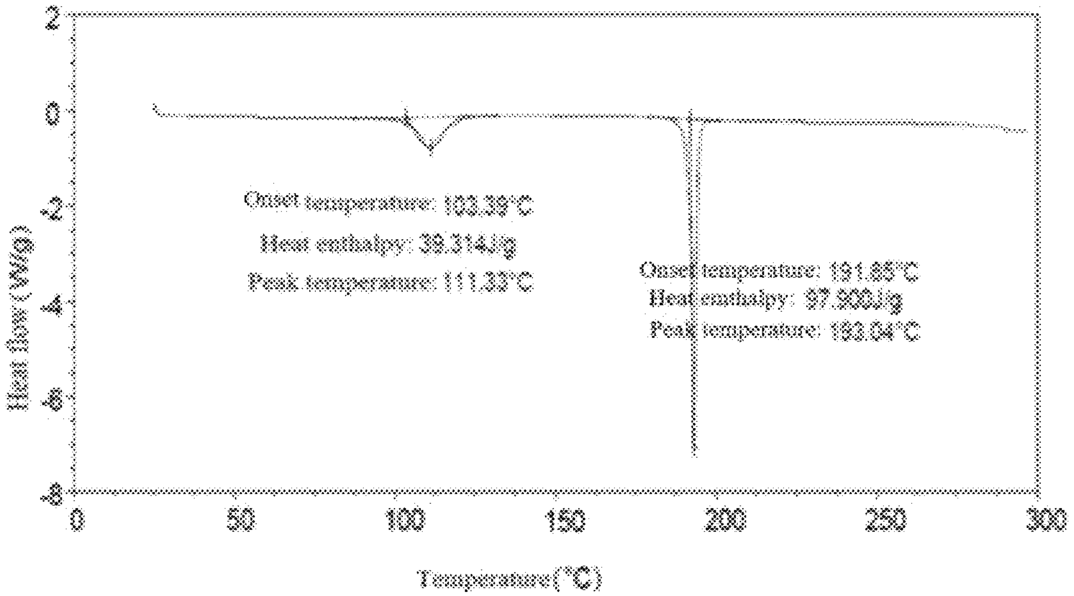
FIG. 9 is the Differential Scanning Calorimetry diagram of the crystal form III of the compound as represented by formula A.

DSC showed that the crystal form III had an endothermic peak with onset temperature of 103.39 °C and peak temperature of 111.33 °C; and an endothermic peak with onset temperature of 191.85 °C and peak temperature of 193.04 °C, and the DSC graph was shown in FIG. 9.

Figure 10:
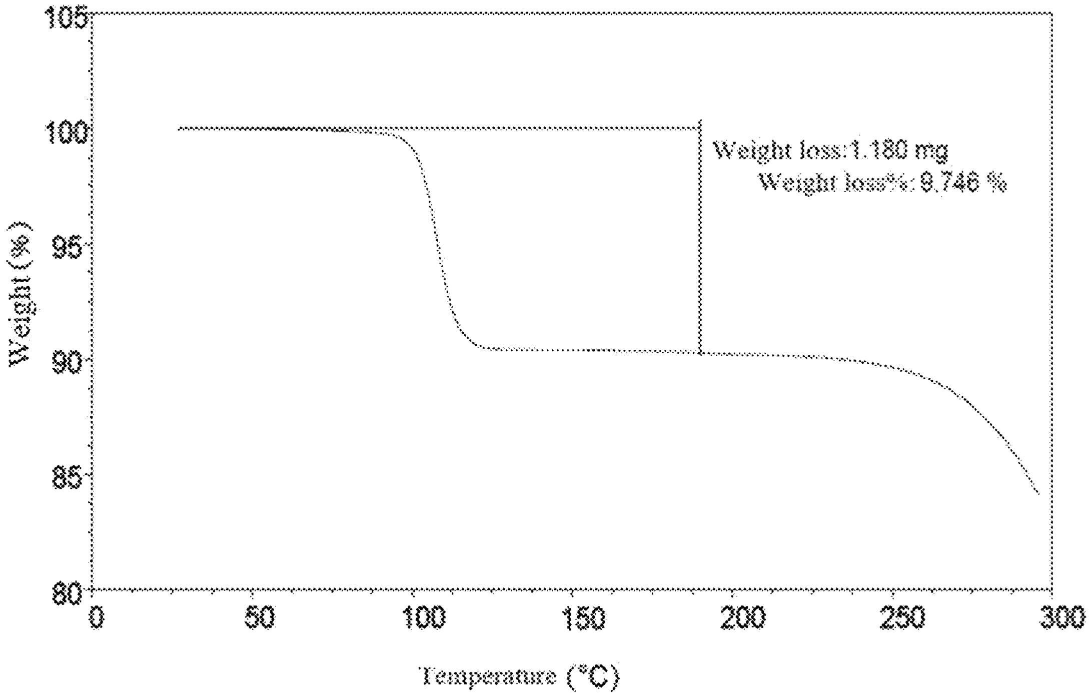
FIG. 10 is the Thermogravimetric Analysis plot of the crystal form III of the compound as represented by formula A.

TGA showed that the crystal form III lost 9.746% by weight of volatiles when heated to about 190 °C, and the weight loss incurred above 190 °C was due to decomposition, and its TGA graph was shown in FIG. 10.

Figure 11:
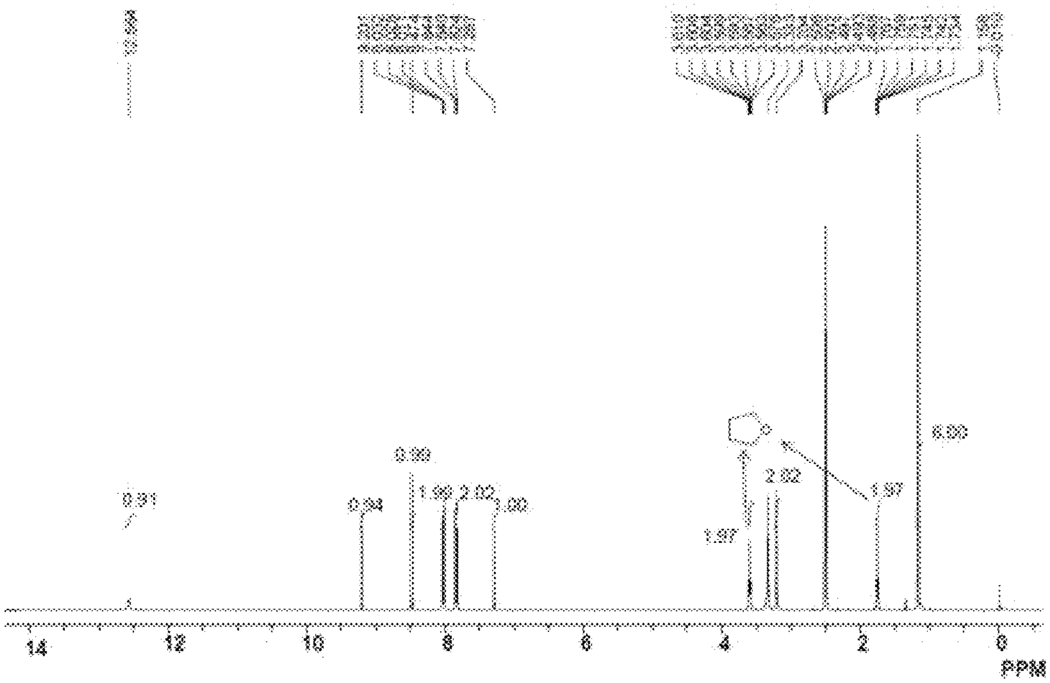
FIG. 11 the liquid nuclear magnetic hydrogen spectrum of the crystal form III of the compound as represented by formula A.

The $^1H$ NMR spectrum of the crystal form III was shown in FIG. 11. Compared with the $^1H$ NMR spectrum of crystal form I (FIG. 7), a peak with an integral value of 1.97 appeared at a chemical shift of 1.76 ppm, which was determined to be a characteristic peak of the four hydrogens of the methylene group ($-CH_2-$) of tetrahydrofuran based on the chemical shift, and a peak with an integral value of 1.97 appeared at 3.60 ppm, which was determined to be a characteristic peak of the four hydrogens of the methylene ($-CH_2O-$) of tetrahydrofuran, since the six hydrogens in the two methyl groups ($-CH_3$) of the compound as represented by formula A are known to peak at 1.17 ppm with an integral value of 6.00, thus it is deduced about 0.5 mole of tetrahydrofuran was combined in the crystal form III.

Analyzed by reversed phase HPLC, purity of the compound as represented by formula A in the crystal form III was 99.1%, and content of the unknown impurity with an RRT of about 0.62 was 0.15%.

Example 13

Preparation of the Crystal Form VI of the Compound as Represented by Formula A A suspension of 1.0 g of the crude product of the compound as represented by formula A prepared in Example 11 in 10 mL of 1,4-dioxane—was refluxed at 105±5 °C, stirred to obtain a hot and clear solution, which was immediately placed into a refrigerator at −20 °C for 3 days, and the solid was filtered out at room temperature, and dried under reduced pressure at 60 °C for 2 hours to obtain 0.65 g of a white solid at a yield of 65.3%.

The resulting solid was the crystal form VI of the compound as represented by formula A, and its X-ray Powder Diffraction pattern was shown in FIG. 12, and data of 2θ angle, d-spacing and relative intensity of peak height of the major diffraction peaks of the solid in the X-ray Powder Diffraction pattern expressed in terms of the 2θ angle was shown in Table 5 below:

TABLE 5

| Number | 2θ (°) | d-spacing (Å) | relative intensity of peak height (%) |
|---|---|---|---|
| 1 | 6.299 | 14.02 | 100.0 |
| 2 | 12.742 | 6.94 | 25.8 |
| 3 | 14.143 | 6.26 | 2.3 |
| 4 | 14.599 | 6.06 | 3.7 |
| 5 | 15.470 | 5.72 | 2.0 |
| 6 | 16.555 | 5.35 | 1.6 |
| 7 | 17.284 | 5.13 | 7.1 |
| 8 | 17.836 | 4.97 | 4.3 |
| 9 | 18.180 | 4.88 | 1.0 |
| 10 | 19.121 | 4.64 | 8.8 |
| 11 | 19.538 | 4.54 | 12.4 |
| 12 | 21.249 | 4.18 | 1.4 |
| 13 | 22.362 | 3.97 | 4.5 |
| 14 | 23.488 | 3.78 | 2.8 |
| 15 | 24.161 | 3.68 | 2.8 |
| 16 | 24.556 | 3.62 | 4.3 |
| 17 | 25.207 | 3.53 | 5.1 |
| 18 | 26.810 | 3.32 | 1.2 |
| 19 | 29.593 | 3.02 | 1.2. |

Figure 13:
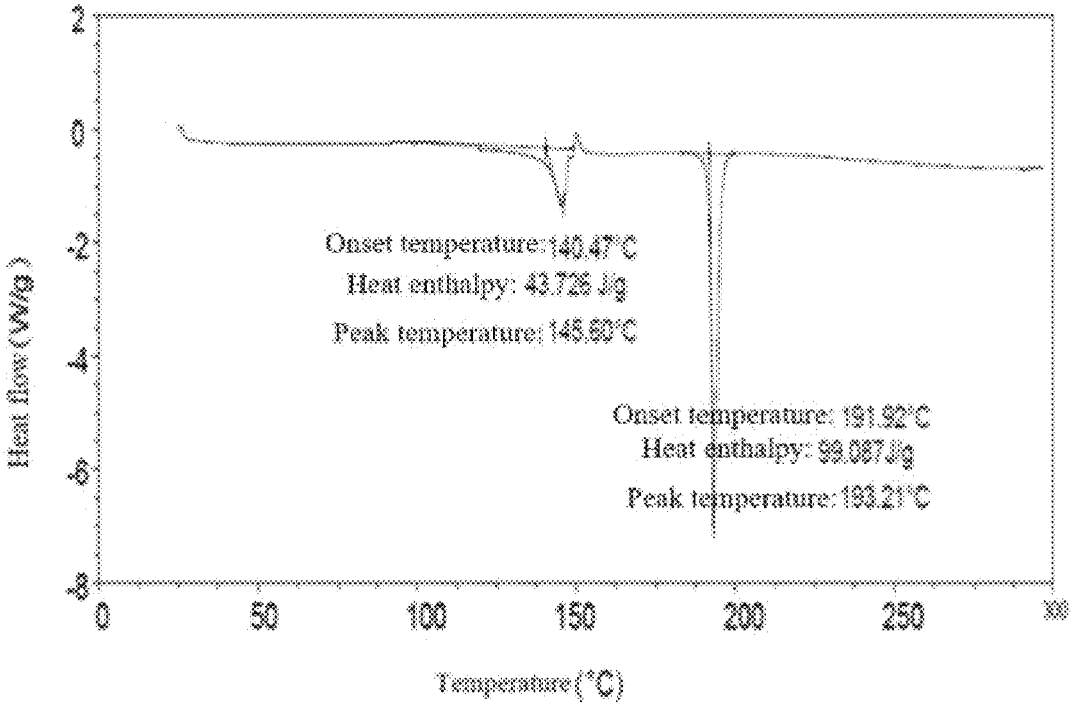
FIG. 13 is the Differential Scanning Calorimetry diagram of the crystal form VI of the compound as represented by formula A.

DSC showed that the crystal form VI had an endothermic peak with onset temperature of 140.47 °C and peak temperature of 145.60 °C; and an endothermic peak with onset temperature of 191.92 °C and peak temperature of 193.21 °C, and its DSC graph was shown in FIG. 13.

Figure 14:
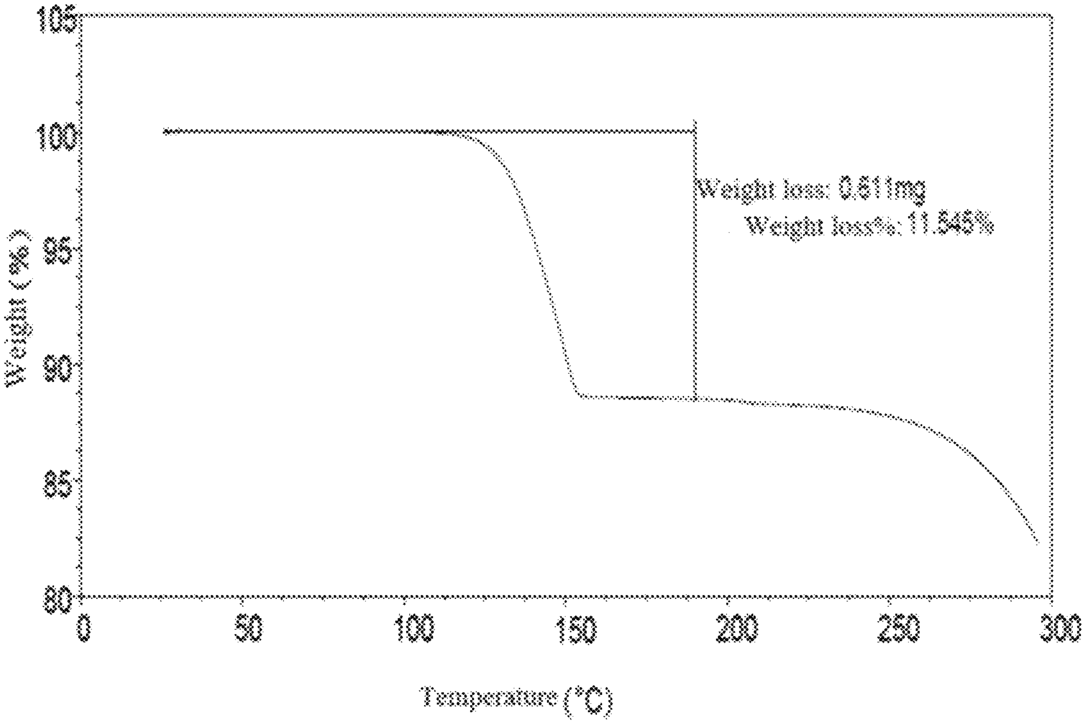
FIG. 14 is the Thermogravimetric Analysis plot of the crystal form VI of the compound as represented by formula A.

TGA showed that the crystal form VI lost 11.545% by weight of volatiles when heated to about 190 °C, and the weight loss above 190 °C was due to decomposition, and its TGA graph was shown in FIG. 14.

Figure 15:
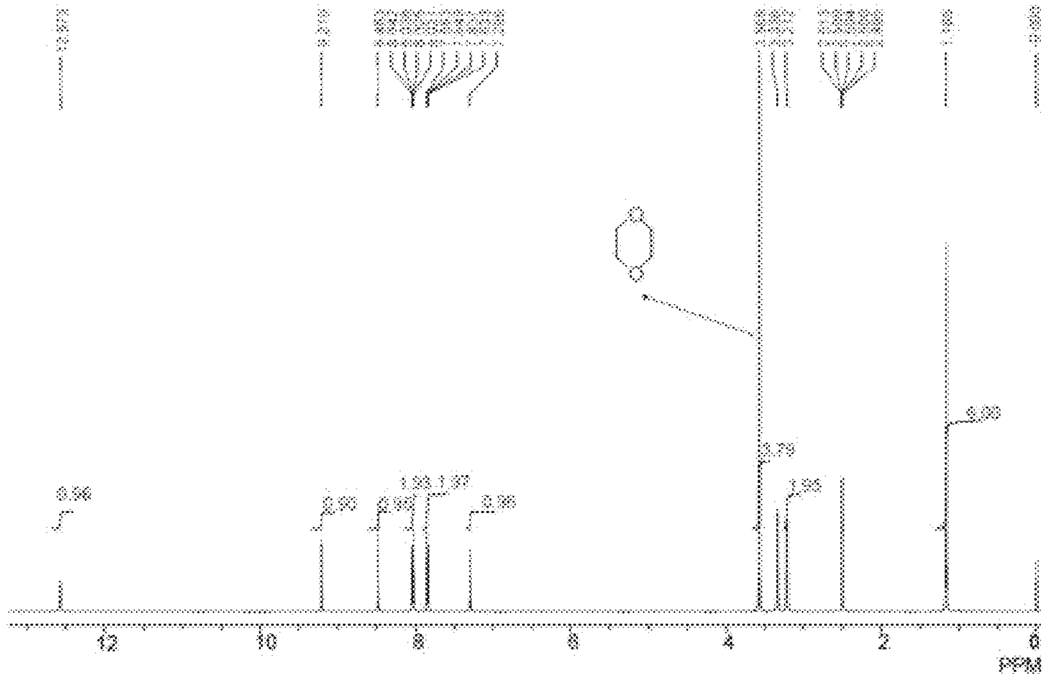
FIG. 15 is the liquid nuclear magnetic hydrogen spectrum of the crystal form VI of the compound as represented by formula A.

The $^1$H NMR spectrum of the crystal form VI was shown in FIG. 15. Compared with the $^1$H NMR spectrum of the crystal form I (FIG. 7), a peak with an integral value of 3.79 appeared at a chemical shift of 3.57 ppm on $^1$H NMR spectrum of the crystal form VI, which was determined to be a characteristic peak of four methylidenes ($—CH_2—$) with eight hydrogens of the 1,4-dioxane ring on the basis of the shifts, since it is known that the six hydrogens of two methyls ($—CH_3$) of the compound as represented by Formula A are present at 1.17 ppm with an integral value of 6.00. Thus it was deduced that about 0.5 mole of 1,4-dioxane was combined in the crystal form VI.

Analyzed by reversed phase HPLC, the purity of the compound as represented by formula A in the crystal form VI was 99.6%, and content of the unknown impurity with an RRT of about 0.62 was 0.13%.

Example 14

Preparation of the Crystal Form IV of the Compound as Represented by Formula A 1.0 g of the crude product of the compound as represented by formula A prepared in Example 11 was added into 20 mL of 1,4-dioxane and stirred at about 80 °C until the resulting mixture was nearly clear, filtered rapidly while hot through a 0.45 μ m nylon filter membrane, and the filtrate was slowly reduced to room temperature at a rate of 5 °C/h. The solid was filtered out, and dried under reduced pressure at 40 °C overnight to give 0.50 g of a white solid at a yield of 50.0%.

Figure 16:
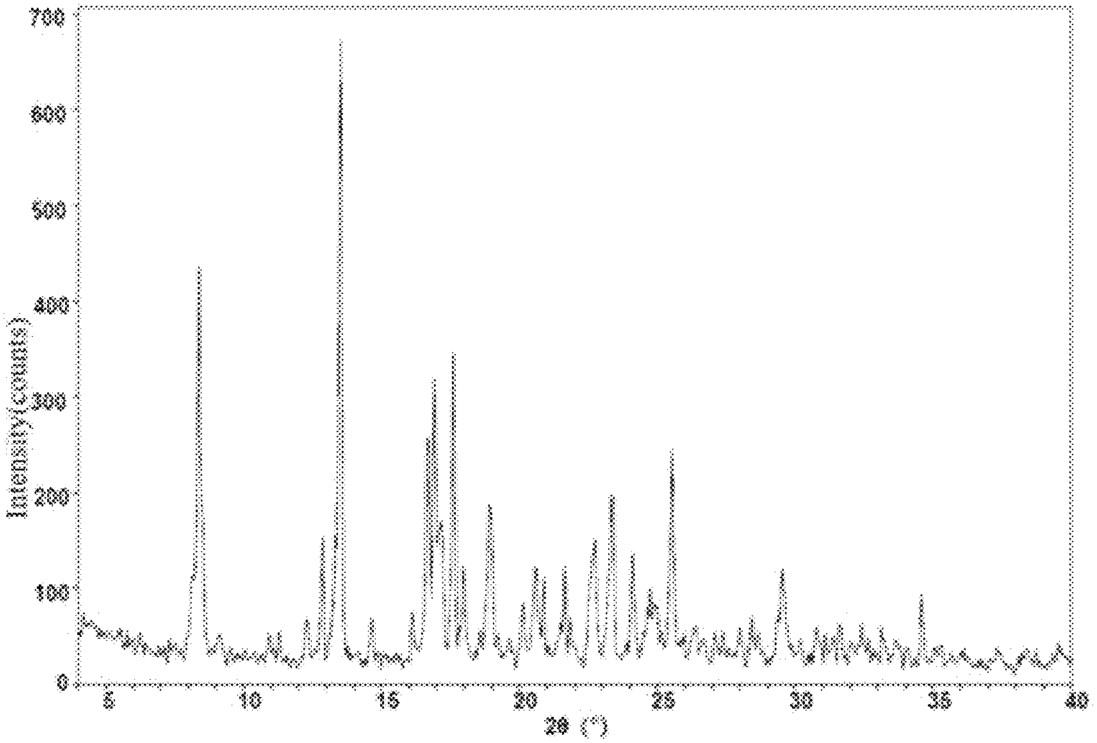
FIG. 16 is the X-ray Powder Diffraction pattern of the crystal form IV of the compound as represented by formula A.

The resulting solid was the crystal form IV of the compound as represented by formula A, and its X-ray Powder Diffraction pattern was shown in FIG. 16, and data of 2θ angle, d-spacing, and relative intensity of peak height for the major diffraction peaks of the solid in the X-ray Powder Diffraction pattern expressed at a 2θ angle was shown in Table 6 below.

TABLE 6

| Number | 2θ (°) | d-spacing (Å) | relative intensity of peak height (%) |
|---|---|---|---|
| 1 | 8.391 | 10.53 | 61.8 |
| 2 | 12.293 | 7.19 | 6.9 |
| 3 | 12.848 | 6.88 | 18.0 |
| 4 | 13.508 | 6.55 | 100.0 |
| 5 | 14.647 | 6.04 | 6.5 |
| 6 | 16.119 | 5.49 | 6.3 |
| 7 | 16.682 | 5.31 | 36.2 |
| 8 | 16.945 | 5.23 | 27.4 |
| 9 | 17.153 | 5.17 | 20.0 |
| 10 | 17.605 | 5.03 | 48.5 |
| 11 | 17.968 | 4.93 | 14.5 |
| 12 | 18.920 | 4.69 | 24.3 |
| 13 | 20.141 | 4.41 | 8.3 |
| 14 | 20.595 | 4.31 | 13.7 |
| 15 | 20.880 | 4.25 | 11.7 |
| 16 | 21.639 | 4.10 | 14.2 |
| 17 | 22.728 | 3.91 | 18.8 |
| 18 | 23.354 | 3.81 | 24.6 |
| 19 | 24.112 | 3.69 | 14.9 |
| 20 | 24.737 | 3.60 | 8.6 |
| 21 | 25.535 | 3.49 | 30.8 |
| 22 | 29.538 | 3.02 | 14.5 |
| 23 | 34.593 | 2.59 | 10.0. |

Figure 17:
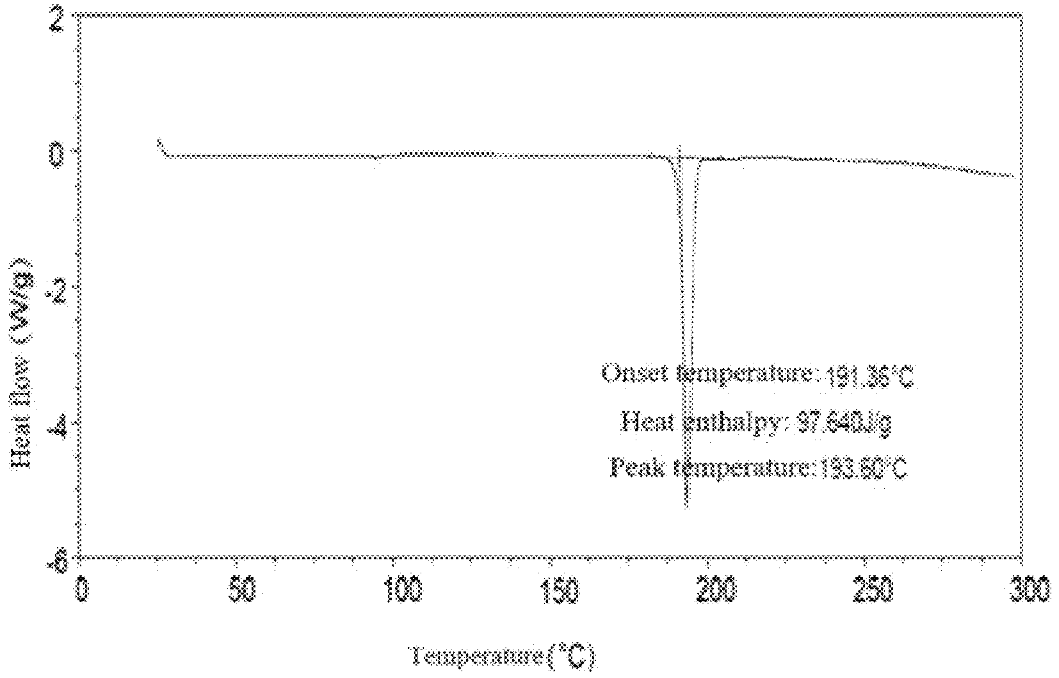
FIG. 17 is the Differential Scanning Calorimetry diagram of the crystal form IV of the compound as represented by formula A.

DSC showed that the crystal form IV had an endothermic peak with onset temperature of 191.36 °C and peak temperature of 193.60 °C, and its DSC graph was shown in FIG. 17.

Figure 18:
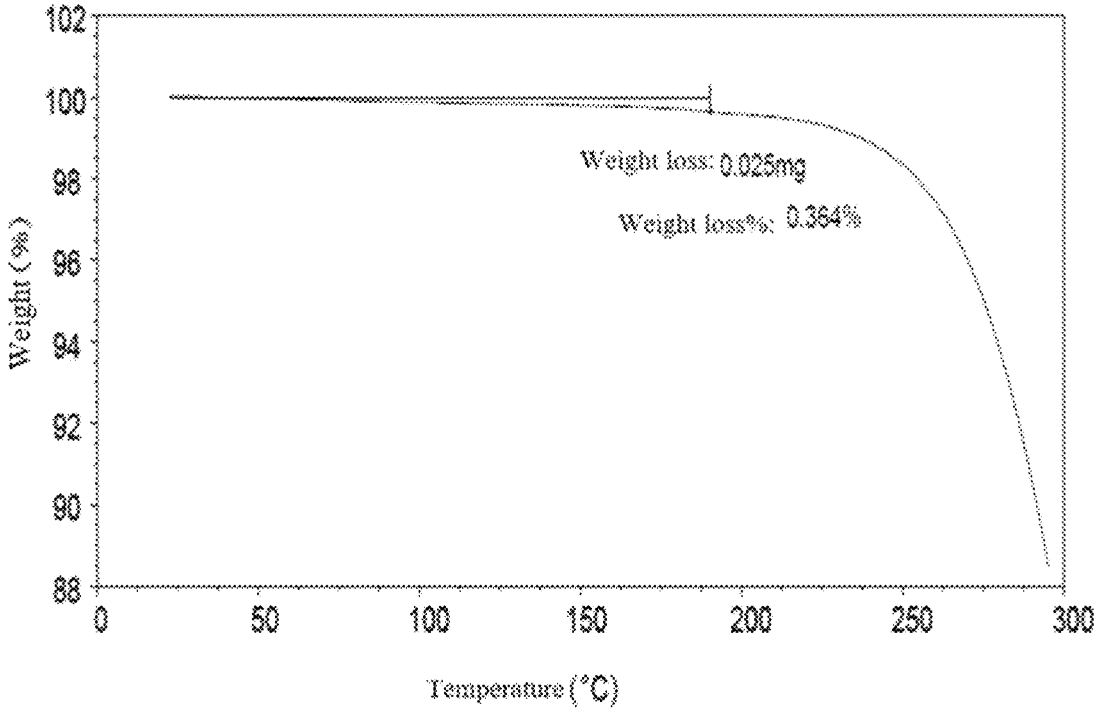
FIG. 18 is the Thermogravimetric Analysis plot of crystal form IV of compound as represented by formula A.

TGA showed that the crystal form IV lost 0.364% by weight of volatiles when heated to about 190 °C, and the weight loss above 190 °C was due to decomposition, and its TGA graph was shown in FIG. 18.

According to the residual solvent determination method (Chinese Pharmacopoeia 2020 edition <0861>), 1,4-dioxane residue in the crystal form IV analyzed by GC was in accordance with the specified limit (should not exceed 0.038%).

The water content in the crystal form IV determined by Karl Fischer method was 0.3%, confirming that the crystal form IV was another anhydrous solid form of the compound as represented by formula A.

Purity of the compound as represented by formula A in the crystal form IV analyzed by reversed-phase HPLC was 99.7%, and content of the unknown impurity with an RRT of about 0.62 was 0.12%.

Example 15

Heating Experiments

About 50 mg each of the samples of the crystal form I, III, VI and IV of the compound as represented by formula A obtained in Examples 11, 12, 13 and 14, respectively, were spread flat in a clean glass dish, heated in a constant temperature oven at 105 °C for about 1 hour and then taken out and immediately tested for XRPD.

Conclusion: The XRPD of the samples of the crystal form I and the crystal form IV unchanged after being heated at 105 °C respectively compared to those before heating.

After comparing, The XRPD pattern of the samples of the crystal form III and the crystal form VI after being heated at 105 °C, respectively, were both consistent with the XRPD pattern of the crystal form I of the compound as represented by formula A described in the present disclosure, confirming that the crystal form III and the crystal form VI would transform to the crystal form I of the compound as represented by formula A by desolvation after being heated and that neither of the crystal form III and the crystal form VI was as stable as the crystal form I under being heated.

Example 16

Stability

1 Stability of the Crystal Form I and the Crystal Form IV of the Compound as Represented by Formula A in Solvent 1.1 Stability Experiment of the Crystal Form I of the Compound as Represented by Formula A in Solvent at Room Temperature About 30 mg of the crystal form I of the compound as represented by formula A was mixed in 1 mL of solvent, dispersed by sonication to make a slurry, suspended and equilibrated at room temperature for a period of time (7 or 14 days), during which time it was ensured that the solid in the vials was always in excess, centrifuged, and the solid was collected and tested for XRPD after evaporation of the solvent to dryness at room temperature.

Conclusion: In the present disclosure, the crystal form I, at room temperature, was stable in a wide range of single solvent or mixed solvents, such as: methanol, ethanol, isopropanol, n-butanol, acetone, 2-butanone, methyl isobutyl ketone, methylene chloride, 2-methyltetrahydrofuran, acetonitrile, n-heptane, n-hexane, cyclohexane, cyclopentane, n-pentane, isopropyl ether, methyl tertiary-butyl ether, ethyl acetate or isopropyl acetate could remain the crystal form unchanged after 7 days of suspension and equilibrium at room temperature; the crystal form could also remain unchanged after 14 days of suspension equilibrium at room temperature in water, methanol-water mixtures (volume ratio of 90:10, 75:25, 45:55, and 10:90, respectively), ethanol-water mixtures (volume ratio of 95:5, 90:10, 65:35- and 15:85, respectively), isopropanol-water mixtures (95:5, 85:15, and 15:85, respectively), and acetone-water mixtures (95:5, 85:15 and 15:85, respectively).

1.2 Stability Experiment of the Crystal Form I of the Compound as Represented by Formula A in Solvent at High Temperature About 50 mg of the crystal form I of the compound as represented by formula A was mixed in 1 mL of solvent, dispersed ultrasonically to make a slurry, and placed in a constant temperature shaker at 50 °C for shaking and equilibrium, during which it was ensured that there was always an excess of solids in the vials, and then centrifuged the slurry after equilibrium for a certain period of time, and then the solids were collected and tested for XRPD after the solvent was evaporated to dryness at room temperature.

Conclusion: In the present disclosure, the stability of the crystal form I as described, was good in a variety of single solvent or mixtures of solvents at 50 °C, e.g., the crystal form could remain unchanged after 43 days of suspension equilibration in methanol, ethanol, isopropanol, acetone or ethyl acetate, and the crystal form could also remain unchanged after 30 days of suspension equilibration in methanol-water, ethanol-water, isopropanol-water and acetone-water, all at the ratio of 50:50

1.3 Competition Experiments of the Crystal Forms I and the Crystal Form IV of the Compound as Represented by Formula a in Solvents at Room Temperature Approximately 15 mg of the crystal form I of the compound as represented by formula A and 15 mg of the crystal form IV of the compound as represented by formula A were mixed in 1 mL of solvent, respectively, and ultrasonically dispersed to make a slurry, which was suspended and equilibrated at room temperature, during which time it was ensured that the solids in the vials were always in excess, and then centrifuged after 7 days, and the solids were collected and tested for XRPD after the solvent was evaporated to dryness at room temperature.

Conclusion: In the present disclosure, after 7 days of competition between the crystal form I and crystal form IV in each solvent at room temperature, both of the solids transformed to the crystal form I, confirming that the stability of the crystal form I is superior to that of the crystal form IV. The tested solvents were methanol, ethanol, isopropanol, n-butanol, acetone, 2-butanone, methyl isobutyl ketone, methylene chloride, 2-methyltetrahydrofuran, acetonitrile, n-heptane, n-hexane, cyclohexane, cyclopentane, n-pentane, isopropyl ether, methyl tert-butyl ether, ethyl acetate, or isopropyl acetate.

2 Stability of the Crystal Form I of the Compound as Represented by Formula A Under Conditions of High Temperature, High Humidity and Light Sample of the crystal form I of the compound as represented by formula A prepared in Example 11 was subjected to an influencing factor stability test consisting of high temperature, high humidity and light, and the indexes examined included total impurities, water content, assay and polymorph identification, the detailed experimentation was as follows:

An appropriate amount of the crystal form I sample of the compound as represented by formula A was laid flat in a clean glass dish and placed openly under conditions of high temperature (60±2 °C), high humidity (25 °C, RH92.5±5%) and light (4500±500 Lux, 25 °C), respectively. Samples were taken and tested at 5 and 10 days and the results were shown in Tables 7-9 below:

TABLE 7

Test results of influencing factor of high temperature (60 ± 2 °C)

| | Time | | |
|---|---|---|---|
| Items | 0 day | 5 days | 10 days |
| Total impurities | 0.05% | 0.07% | 0.07% |
| Water content | 0.05% | 0.04% | 0.04% |

TABLE 7-continued

| Test results of influencing factor of high temperature (60 ± 2 °C) | | | |
|---|---|---|---|
| | Time | | |
| Items | 0 day | 5 days | 10 days |
| Assay | 99.1% | 101.1% | 100.0% |
| Polymorph | Crystal form I | Crystal form I | Crystal form I |

TABLE 8

| Test results of influencing factor of high humidity (25 °C, RH92.5 ± 5%) | | | |
|---|---|---|---|
| | Time | | |
| Items | 0 day | 5 days | 10 days |
| Total impurities | 0.05% | 0.07% | 0.07% |
| Water content | 0.05% | 0.06% | 0.09% |
| Assay | 99.1% | 100.1% | 100.6% |
| Polymorph | Crystal form I | Crystal form I | Crystal form I |

TABLE 9

| Test results of influencing factor of light (4500 ± 500 Lux, 25 °C) | | | |
|---|---|---|---|
| | Time | | |
| Items | 0 day | 5 days | 10 days |
| Total impurities | 0.05% | 0.07% | 0.12% |
| Water content | 0.05% | 0.04% | 0.09% |
| Assay | 99.1% | 99.8% | 100.3% |
| Polymorph | Crystal form I | Crystal form I | Crystal form I |

Note:

Assay determination method: according to high performance liquid chromatography method (Chinese Pharmacopoeia 2020 Edition <0512> Method No. 2), the chromatographic conditions were as follows: octadecylsilane-bonded silica gel was used as filler (SunFire C18, 3.5 μm, 4.6*150 mm), the mobile phase A was water containing 0.05% trifluoroacetic acid, the mobile phase B was acetonitrile containing 0.05% trifluoroacetic acid, isocratic elution by A: B=77:23, flow rate was 1.0 mL/min, and the detection wavelength was 230 nm, and the column temperature was 30 °C. Methanol: water containing 0.05% trifluoroacetic acid=40:60 (v/v) was used as diluent to prepare the test sample solution and standard sample solution with concentration of 0.1 mg/mL, and 10 μL of each solution was injected into the liquid chromatograph to record the chromatogram, respectively. According to the external standard method by peak area and calculating on anhydrous material, the test sample should contain 98.0% to 102.0% of the compound as represented by formula A.

Conclusion: The data in Table 7-9 above showed that the crystal form I was placed in the condition of high temperature (60=2 °C), high humidity (25 °C, RH92.5±5%) and light (4500±500 Lux, 25 °C) for 10 days, there is no significant change for the assessment indexes when compared with the sample before influence factor test treatment, stability of the crystal form I is good.

3 Stability of the Crystal Form I of the Compound as Represented by Formula A in Accelerated Condition The sample of the crystal form I of the compound as represented by formula A prepared in Example 11 was taken for the stability test under accelerated condition, and the indexes examined included total impurities, water content, assay and polymorph identification, and the detailed experimentation was as follows:

Sample of the crystal form I of the compound as represented by formula A was sealed in a pharmaceutical low density polyethylene bag, and then sealed in a polyester/aluminum/polyethylene composite bag for pharmaceutical packaging use, and then stored in the condition of accelerated stability (40±2 °C, RH 75±5%). Samples were tested at 1, 2, 3 and 6 months and the results were shown in Table 10 below:

TABLE 10

| Test results of the accelerated stability (40 ± 2 °C, RH 75 ± 5%) | | | | | |
|---|---|---|---|---|---|
| | Time | | | | |
| Items | 0 day | 1 month | 2 months | 3 months | 6 months |
| Total impurities | 0.05% | 0.05% | 0.03% | 0.03% | 0.05% |
| Water content | 0.04% | 0.06% | 0.03% | 0.04% | 0.10% |
| Assay | 99.1% | 99.2% | 98.6% | 98.5% | 99.7% |
| Polymorph | Crystal form I | Crystal form I | Crystal form I | Crystal form I | Crystal form I |

Conclusion: the data in the above table 10 showed that the crystal form I stored in the condition of accelerated stability (40 ± 2 °C, RH 75 ± 5%) for 6 months, there is no significant change for the assessment indexes compared with the sample before the accelerated test treatment, stability of the crystal form I is good.

It should be understood that the embodiments described herein are for illustrative purpose only, and various improvements or variations in view of this will be suggested to those skilled in the art, and they are included within the subject matter and scope of the present application and the scope of the appended claims. All publications, patents and patent applications cited herein are incorporated herein by reference and used for all purposes.

What is claimed is:

1. A crystal form I of a compound as represented by formula A having an X-ray Powder Diffraction pattern comprising diffraction peaks at angles 2θ of 8.3±0.2°, 12.8±0.2°, 13.4±0.2°, 17.5±0.2°, 17.9±0.2° and 23.3±0.2°, the X-ray Powder Diffraction is measured by Cu K-alpha radiation;

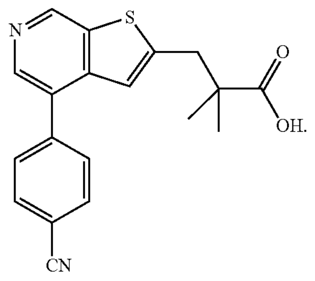

A

2. A method of preparing the crystal form I of the compound as represented by formula A according to claim 1, which is solution 1 or solution 2;

solution 1: at 60-75 °C, cooling a mixture of the compound as represented by formula A, THF and anti-solvent, crystalizing and filtrating; the anti-solvent is methanol and/or water;

solution 2: at 60-70 °C, cooling a solution formed by a crystal form III and/or VI of the compound as represented by formula A and a solvent, precipitating and filtrating; the solvent is a mixed solvent of THF and isopropanol;

the crystal form III of the compound as represented by formula A having an X-ray Powder Diffraction pattern comprising diffraction peaks at angles 2θ of 6.7±0.2°, 13.6±0.2°, 14.5±0.2°, 15.3±0.2°, 15.8±0.2°, 16.1±0.2°, 16.8±0.2°, 17.1±0.2°, 19.0±0.2°, 19.6±0.2°, 20.3±0.2° and 22.6±0.2°, the X-ray Powder Diffraction is measured by Cu K-alpha radiation;

the crystal form VI of the compound as represented by formula A having an X-ray Powder Diffraction pattern comprising diffraction peaks at angles 2θ of 6.3±0.2°, 12.7±0.2°, 14.1±0.2°, 14.6±0.2°, 17.3±0.2°, 17.8±0.2°, 19.1±0.2°, 19.5±0.2°, 22.4±0.2°, 24.6±0.2° and 25.2±0.2°, the X-ray Powder Diffraction is measured by Cu K-alpha radiation.

3. The method of preparing the crystal form I of the compound as represented by formula A according to claim 2, wherein, in solution 1, the volume-to-mass ration of the THF to the compound as represented by formula A is 3.0-30.0 mL/g;

and/or, in solution 1, the mixture is obtained by adding the compound as represented by formula A into a mixed solvent of THF and the anti-solvent, or by addition of the anti-solvent after the compound as represented by formula A was dissolved in THF;

and/or, in solution 1, the volume ratio of THF to the anti-solvent is 0.5:1-5:1;

and/or, in solution 1, temperature of the cooling is −20 to 20 °C;

and/or, in solution 1, speed of the cooling is 5-30 °C/h;

and/or, in solution 1, the filtrating is performed under reduced pressure;

and/or, in solution 1, a post-treatment step of drying is performed after the filtrating;

and/or, in solution 2, temperature of the cooling is −20 to 20 °C;

and/or, in solution 2, speed of the cooling is 5 to 30 °C/h;

and/or, in solution 2, the filtrating is performed under reduced pressure;

and/or, in solution 2, a post-treatment step of drying is performed after the filtrating;

and/or, in solution 2, in the mixed solvent, volume ration of THF to isopropanol is 0.5:1 to 2:1;

and/or, in solution 2, the crystal form III of the compound as represented by formula A is obtained by method comprising the following steps, removing the solvent from a solution of the compound as represented by formula A in THF;

and/or, in solution 2, the crystal form VI of the compound as represented by formula A is obtained by method of preparation comprising the following steps, cooling a solution of the compound as represented by formula A in 1,4-dioxane to −10 to −20 °C, filtrating, and drying.

4. The method of preparing the crystal form I of the compound as represented by formula A according to claim 3, wherein, in solution 1, when the anti-solvent is methanol, the volume ratio of THF to the anti-solvent is 0.5:1 to 2:1;

and/or, in solution 1, when the anti-solvent is water, the volume ratio of THF to the anti-solvent is 0.5:1 to 5:1;

and/or, in solution 1, the cooling includes mixing the mixture with isopropanol, then cooling;

and/or, in solution 1, the drying is performed at 65 °C under reduced pressure, the time of the drying is 1 hour to 3 days;

and/or, in solution 2, in the method of preparing the crystal form III of the compound as represented by formula A, the removing is performed by way of distillation;

and/or, in solution 2, in the method of preparing the crystal form III of the compound as represented by formula A, the removing of the solvent is preceded by filtrating the solution of the compound as represented by formula A in THF;

and/or, in solution 2, the crystal form III of the compound as represented by formula A, measured by Cu K-alpha radiation, having an X-ray Powder Diffraction pattern comprising diffraction peaks with data of diffraction angles 2θ, d-spacing and relative intensity of peak height as shown in Table 4:

TABLE 4

| Number | 2θ(±0.2°) | d-spacing(Å) | Relative intensity of peak height (%) |
|---|---|---|---|
| 1 | 6.729 | 13.13 | 100.0 |
| 2 | 13.601 | 6.51 | 39.9 |
| 3 | 14.527 | 6.09 | 11.3 |
| 4 | 15.280 | 5.79 | 5.3 |
| 5 | 15.653 | 5.66 | 3.4 |
| 6 | 15.832 | 5.59 | 5.4 |
| 7 | 16.133 | 5.49 | 2.7 |
| 8 | 16.822 | 5.27 | 3.4 |
| 9 | 17.138 | 5.17 | 8.1 |
| 10 | 17.317 | 5.12 | 5.9 |
| 11 | 18.954 | 4.68 | 11.9 |
| 12 | 19.646 | 4.52 | 13.3 |
| 13 | 20.323 | 4.37 | 33.2 |
| 14 | 20.798 | 4.27 | 4.0 |
| 15 | 22.371 | 3.97 | 5.1 |
| 16 | 22.632 | 3.93 | 6.0 |
| 17 | 23.149 | 3.84 | 3.7 |
| 18 | 24.727 | 3.60 | 3.2; |

and/or, in solution 2, in the method of preparing the crystal form VI of the compound as represented by formula A, temperature of the solution formed by the compound as represented by formula A with 1,4-dioxane is 40-120 °C;

and/or, in solution 2, in the method of preparing the crystal form VI of the compound as represented by formula A, the cooling is fast cooling;

and/or, in solution 2, in the method of preparing the crystal form VI of the compound as represented by formula A, the filtrating is performed under reduced pressure;

and/or, in solution 2, in the method of preparing the crystal form VI of the compound as represented by formula A, the drying is performed under reduced pressure;

and/or, in solution 2, the crystal form VI of the compound as represented by formula A, measured by Cu K-alpha radiation, having an X-ray Powder Diffraction pattern comprising diffraction peaks with data of diffraction angles 2θ, d-spacing and relative intensity of peak height as shown in Table 5:

TABLE 5

| Number | 2θ(±0.2°) | d-spacing(Å) | Relative intensity of peak height (%) |
|---|---|---|---|
| 1 | 6.299 | 14.02 | 100.0 |
| 2 | 12.742 | 6.94 | 25.8 |
| 3 | 14.143 | 6.26 | 2.3 |
| 4 | 14.599 | 6.06 | 3.7 |
| 5 | 15.470 | 5.72 | 2.0 |
| 6 | 16.555 | 5.35 | 1.6 |
| 7 | 17.284 | 5.13 | 7.1 |
| 8 | 17.836 | 4.97 | 4.3 |
| 9 | 18.180 | 4.88 | 1.0 |
| 10 | 19.121 | 4.64 | 8.8 |
| 11 | 19.538 | 4.54 | 12.4 |
| 12 | 21.249 | 4.18 | 1.4 |
| 13 | 22.362 | 3.97 | 4.5 |
| 14 | 23.488 | 3.78 | 2.8 |
| 15 | 24.161 | 3.68 | 2.8 |
| 16 | 24.556 | 3.62 | 4.3 |
| 17 | 25.207 | 3.53 | 5.1 |
| 18 | 26.810 | 3.32 | 1.2 |
| 19 | 29.593 | 3.02 | 1.2. |

Figure 12:
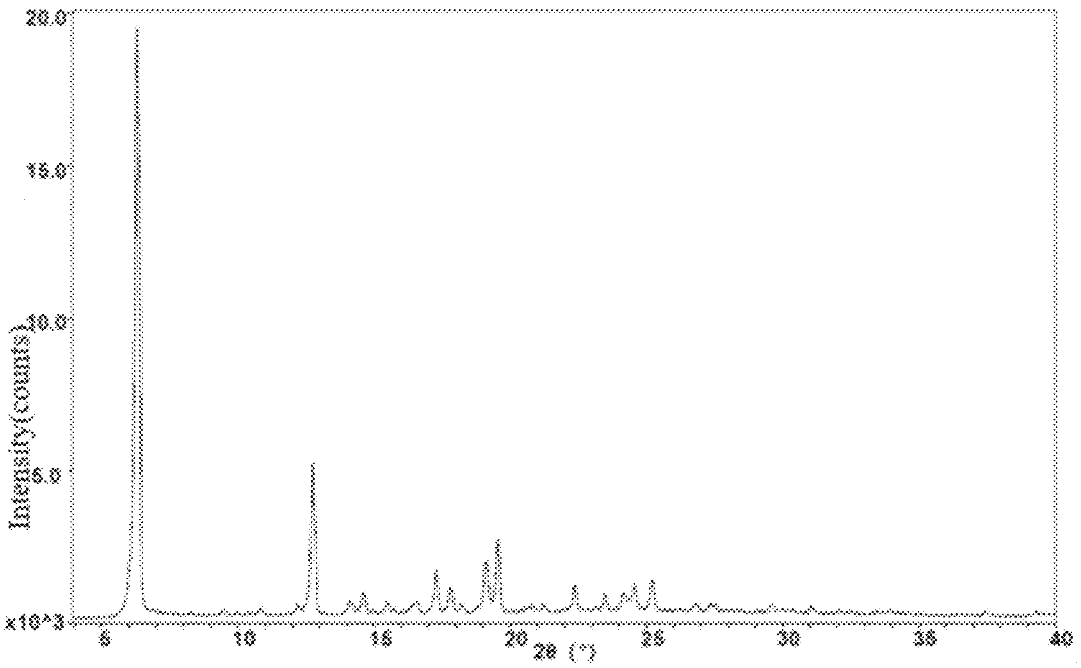
FIG. 12 is the X-ray Powder Diffraction pattern of the crystal form VI of the compound as represented by formula A.

5. The method of preparing the crystal form I of the compound as represented by formula A according to claim 4, wherein, measured by Cu K-alpha radiation, the crystal form III of the compound as represented by formula A having an X-ray Powder Diffraction pattern as shown in FIG. 8;

and/or, the crystal form III of the compound as represented by formula A having a Differential Scanning Calorimetry (DSC) graph as shown in FIG. 9;

and/or, the crystal form III of the compound as represented by formula A having a Thermogravimetric Analysis (TGA) graph as shown in FIG. 10;

and/or, the crystal form VI of the compound as represented by formula A, measured by Cu K-alpha radiation, having an X-ray Powder Diffraction pattern as shown in FIG. 12;

and/or, the crystal form VI of the compound as represented by formula A having a Differential Scanning Calorimetry graph as shown in FIG. 13;

and/or, the crystal form VI of the compound as represented by formula A having a Thermogravimetric Analysis graph as shown in FIG. 14.

6. A pharmaceutical composition comprising a therapeutically effective amount of the crystal form I of the compound as represented by formula A according to claim 1 and one or more pharmaceutically acceptable carriers and/or diluents thereof.

7. A pharmaceutical composition comprising a therapeutically effective amount of the crystal form I of the compound as represented by formula A according to claim 1 and other uric acid-lowering drugs; the other uric acid-lowering drug is one or more of a uric acid transporter 1 inhibitor, a xanthine oxidase inhibitor, a xanthine oxidoreductase and a xanthine dehydrogenase inhibitor.

8. A method of treating hyperuricemia or a related disease, the method comprising administrating to a patient in need thereof a therapeutically effective amount of the crystal form I of the compound as represented by formula A according to claim 1; wherein, the related disease of hyperuricemia is selected from one or more of gout, hypertension, diabetes, hypertriglyceridemia, metabolic syndrome, coronary heart disease and kidney damage.

9. A method of inhibiting uric acid transporter 1, the method comprising administrating to a patient in need thereof a therapeutically effective amount of the crystal form I of the compound as represented by formula A according to claim 1.

10. A crystal form I of a compound as represented by formula A having an X-ray Powder Diffraction pattern comprising diffraction peaks at angles 2θ of 8.3±0.2°, 11.2±0.2°, 12.2±0.2°, 12.8±0.2°, 13.4±0.2°, 17.1±0.2°, 17.5±0.2°, 17.9±0.2°, 20.8±0.2°, 21.5±0.2°, 22.4±0.2°, 23.3±0.2°, 24.0±0.2°, 25.4±0.2°, 29.4±0.2° and 34.5±0.2°, the X-ray Powder Diffraction is measured by Cu K-alpha radiation:

A

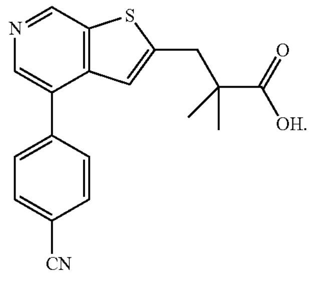

11. A crystal form I of a compound as represented by formula A having an X-ray Powder Diffraction pattern measured by Cu K-alpha radiation, comprising diffraction peaks with data of diffraction angles 2θ, d-spacing and relative intensity of peak height shown in Table 3:

TABLE 3

| Number | 2θ(±0.2°) | d-spacing(Å) | Relative intensity of peak height (%) |
|---|---|---|---|
| 1 | 8.283 | 10.67 | 49.1 |
| 2 | 11.204 | 7.89 | 6.4 |
| 3 | 12.186 | 7.26 | 6.0 |
| 4 | 12.753 | 6.94 | 32.2 |
| 5 | 13.415 | 6.59 | 100.0 |
| 6 | 17.100 | 5.18 | 8.7 |
| 7 | 17.505 | 5.06 | 27.3 |
| 8 | 17.879 | 4.96 | 21.9 |
| 9 | 20.469 | 4.34 | 3.4 |
| 10 | 20.789 | 4.27 | 13.8 |
| 11 | 21.542 | 4.12 | 9.5 |
| 12 | 22.450 | 3.96 | 18.3 |
| 13 | 23.280 | 3.82 | 37.3 |
| 14 | 24.029 | 3.70 | 8.2 |
| 15 | 25.444 | 3.50 | 14.8 |
| 16 | 29.436 | 3.03 | 7.9 |
| 17 | 30.700 | 2.91 | 3.5 |
| 18 | 31.300 | 2.86 | 4.3 |
| 19 | 31.541 | 2.83 | 4.3 |
| 20 | 34.497 | 2.60 | 8.9; |

A

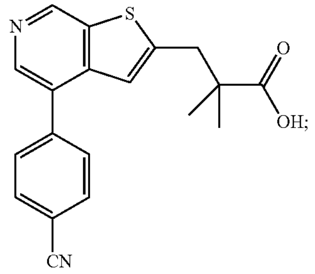

and/or, a crystal form I of a compound as represented by formula A having an infrared absorption spectrum comprising characteristic peaks at 3090 $cm^{-1}$, 3061 $cm^{-1}$, 2965 $cm^{-1}$, 2924 $cm^{-1}$, 2868 $cm^{-1}$, 2222 $cm^{-1}$, 1697 $cm^{-1}$, 1605 $cm^{-1}$, 1578 $cm^{-1}$, 1549 $cm^{-1}$, 1499 $cm^{-1}$, 1474 $cm^{-1}$, 1420 $cm^{-1}$, 1396 $cm^{-1}$, 1296 $cm^{-1}$, 1246 $cm^{-1}$, 1188 $cm^{-1}$, 1051 $cm^{-1}$ and 920 $cm^{-1}$;

and/or, Differential Scanning Calorimetry (DSC) graph of a crystal form I of a compound as represented by formula A having an endothermic peak with onset temperature of 193±2 °C and peak temperature of 195±2 °C;

and/or, a crystal form I of a compound as represented by formula A having a Thermogravimetric Analysis (TGA) graph with no weight loss of volatiles when heated to 190 °C;

and/or, in the Dynamic Vapor Sorption graph of a crystal form I of a compound as represented by formula A, the mass of crystal form I increasing by 0.01% in the relative humidity from 0 to 95% compared with the initial mass.

12. A crystal form I of a compound as represented by formula A, measured by Cu K-alpha radiation, having an X-ray Powder Diffraction pattern as shown in FIG. 2:

A

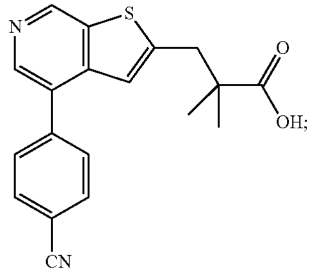

and/or, a crystal form I of a compound as represented by formula A having an infrared absorption spectrum as shown in FIG. 3;

and/or, a crystal form I of a compound as represented by formula A having a Differential Scanning calorimetry (DSC) graph as shown in FIG. 4;

and/or, a crystal form I of a compound as represented by formula A having a Thermogravimetric Analysis (TGA) graph as shown in FIG. 5;

and/or, a crystal form I of a compound as represented by formula A having a Dynamic Vapor Sorption (DVS) graph as shown in FIG. 6.

* * * * *